US011678913B2

(12) United States Patent
Farmer et al.

(10) Patent No.: US 11,678,913 B2
(45) Date of Patent: Jun. 20, 2023

(54) ARTICULATING DEROTATORS FOR DEFORMITY SPINAL SYSTEMS AND METHODS FOR USE THEREOF

(71) Applicant: Zimmer Biomet Spine, Inc., Westminster, CO (US)

(72) Inventors: Heidi Farmer, Lafayette, CO (US); Jared Parker, Denver, CO (US); Chad Coxon, Denver, CO (US)

(73) Assignee: Zimmer Biomet Spine, Inc., Westminster, CO (US)

( * ) Notice: Subject to any disclaimer, the term of this patent is extended or adjusted under 35 U.S.C. 154(b) by 508 days.

(21) Appl. No.: 16/675,885

(22) Filed: Nov. 6, 2019

(65) Prior Publication Data

US 2020/0138480 A1    May 7, 2020

Related U.S. Application Data

(62) Division of application No. 15/683,555, filed on Aug. 22, 2017, now Pat. No. 10,492,837.

(Continued)

(51) Int. Cl.
*A61B 17/70* (2006.01)
*A61B 17/88* (2006.01)
(Continued)

(52) U.S. Cl.
CPC ........ *A61B 17/708* (2013.01); *A61B 17/7077* (2013.01); *A61B 17/7085* (2013.01);
(Continued)

(58) Field of Classification Search
CPC .............. A61B 17/7077; A61B 17/708; A61B 17/7079; A61B 17/8866
See application file for complete search history.

(56) References Cited

U.S. PATENT DOCUMENTS 5,281,223 A    1/1994  Ray
6,090,113 A    7/2000  Le Couedic et al.
(Continued)

FOREIGN PATENT DOCUMENTS

WO    WO-2010045383 A2    4/2010
WO    WO-2018039252 A1    3/2018

OTHER PUBLICATIONS

U.S. Appl. No. 15/683,555 U.S. Pat. No. 10,492,837, filed Aug. 22, 2017, Articulating Derotators for Deformity Spinal Systems and Methods for Use Thereof.
(Continued)

*Primary Examiner* — Ellen C Hammond
(74) *Attorney, Agent, or Firm* — Sheridan Ross P.C.

(57) ABSTRACT

A surgical derotator instrument comprises a shaft, a handle and an articulating coupler. The shaft comprises a first end portion having a bone anchor coupling and a second end portion opposite the first end portion. The handle comprises a body portion and a slot extending in the body portion. The articulating coupler connects the shaft and the handle. A method for coupling a plurality of derotator instruments into a series of derotator instruments comprises: attaching a plurality of derotator instruments to a plurality of adjacent bone anchor housings, each derotator instrument comprising: a shaft for connecting to a bone anchor housing, a handle having a slot, and an adjustable coupler connecting the shaft and the handle; adjusting one or more of the adjustable couplers to align at least one of the slots of the series with other slots of the series; and inserting an elongate member through the at least one slots that are aligned.

18 Claims, 19 Drawing Sheets

Related U.S. Application Data

(60) Provisional application No. 62/377,983, filed on Aug. 22, 2016.

(51) Int. Cl.
*A61B 17/00* (2006.01)
*A61B 17/68* (2006.01)

(52) U.S. Cl.
CPC ...... *A61B 17/7091* (2013.01); *A61B 17/8866* (2013.01); *A61B 17/7082* (2013.01); *A61B 2017/00473* (2013.01); *A61B 2017/00477* (2013.01); *A61B 2017/00862* (2013.01); *A61B 2017/681* (2013.01)

(56) References Cited

U.S. PATENT DOCUMENTS

| | | |
|---|---|---|
| 7,776,072 B2 | 8/2010 | Barry |
| 8,475,467 B2 | 7/2013 | Manninen |
| 8,496,685 B2 | 7/2013 | Landry et al. |
| 8,608,782 B1 | 12/2013 | Rovner |
| 8,672,944 B2 | 3/2014 | Boachie-Adjei et al. |
| 8,936,624 B2 | 1/2015 | Shluzas |
| 9,101,412 B2 | 8/2015 | Bootwala et al. |
| 9,289,244 B2 | 3/2016 | Hestad et al. |
| 9,408,641 B2 | 8/2016 | Zhang et al. |
| 10,098,665 B2 | 10/2018 | Rutschmann et al. |
| 10,492,837 B2 | 12/2019 | Farmer et al. |
| 2006/0122597 A1 | 6/2006 | Jones et al. |
| 2006/0247649 A1 | 11/2006 | Rezach et al. |
| 2007/0213715 A1 | 9/2007 | Bridwell et al. |
| 2007/0213716 A1 | 9/2007 | Lenke et al. |
| 2009/0204159 A1 | 8/2009 | Justis et al. |
| 2010/0042149 A1 | 2/2010 | Chao et al. |
| 2012/0203279 A1 | 8/2012 | Walters et al. |
| 2014/0046374 A1 | 2/2014 | Asaad et al. |
| 2014/0100611 A1 | 4/2014 | Barry |
| 2014/0277170 A1 | 9/2014 | Barrett et al. |
| 2018/0049774 A1 | 2/2018 | Farmer et al. |

OTHER PUBLICATIONS

"U.S. Appl. No. 15/683,555, Non Final Office Action dated Apr. 16, 2019", 9 pgs.

"U.S. Appl. No. 15/683,555, Notice of Allowance dated Jul. 31, 2019", 7 pgs.

"U.S. Appl. No. 15/683,555, Response filed Mar. 11, 2019 to Restriction Requirement dated Jan. 30, 2019", 9 pgs.

"U.S. Appl. No. 15/683,555, Response Filed Jul. 12, 2019 to Non-Final Office Action dated Apr. 16, 2019", 14 pgs.

"U.S. Appl. No. 15/683,555, Restriction Requirement dated Jan. 30, 2019", 7 pgs.

"European Application Serial No. 17758782.1, Communication Pursuant to Article 94(3) EPC dated Dec. 3, 2019", 5 pgs.

"European Application Serial No. 17758782.1, Response to Communication pursuant to Rules 161(1) and 162 EPC filed Oct. 14, 2019", 12 pgs.

"International Application Serial No. PCT/US2017/048045, International Preliminary Report on Patentability dated Mar. 7, 2019", 9 pgs.

"International Application Serial No. PCT/US2017/048045, International Search Report dated Dec. 1, 2017", 7 pgs.

"International Application Serial No. PCT/US2017/048045, Written Opinion dated Dec. 1, 2017", 7 pgs.

Extended Search Report for European Patent Application No. 21174517.9, dated May 9, 2022.

ARTICULATING DEROTATORS FOR DEFORMITY SPINAL SYSTEMS AND METHODS FOR USE THEREOF

CLAIM OF PRIORITY

This application is a divisional of U.S. patent application Ser. No. 15/683,555, filed on Aug. 22, 2017, which claims the benefit of U.S. Provisional Patent Application Ser. No. 62/377,983, filed on Aug. 22, 2016, the benefit of priority of each of which is claimed hereby, and each of which is incorporated by reference herein in its entirety.

TECHNICAL FIELD

The present application pertains generally, but not by way of limitation, to instruments, systems and methods for fixation of bones during orthopedic procedures. More particularly, this disclosure relates to, but not by way of limitation, reduction instruments for spinal realignment procedures, such as derotation instruments or "derotators."

BACKGROUND

The spine is formed of superposed vertebrae, normally aligned along a vertebral axis, from the lumbar vertebrae, through the thoracic vertebrae, and to the cervical vertebrae, each having a posterior wall from which projects a spinous process and two lateral edges from the walls from which project ribs and/or transverse processes and/or lamina, each having a pedicle. If the spine of a person has abnormal curvature, such as from scoliosis, the vertebrae are typically inclined relative to one another and relative to the vertebral axis.

In order to straighten the vertebral column as a remedy for this situation, the lateral edges of the vertebrae on the concave side can be moved away from one another and supported at distances from one another substantially equivalent to the distances between the lateral edges on the other side. Devices known in the art for holding the vertebrae relative to one another include rigid and dynamic stabilization using stiff or flexible rods that are held by rod-receiving elements, such as bone anchors, attached to the vertebrae, for example using screws, hooks, or flexible ligatures.

Assembly of the rods to the rod receiving elements can typically be carried out in the operating room intraoperatively, after the rod-receiving elements have been surgically anchored to an osseous structure of the patient. Once the rods have been positioned, they can be manipulated into a position to straighten the spinal column. In order to facilitate manipulation of the rods, various instruments can be used, such as persuaders and derotators.

Overview

The present inventors have recognized, among other things, that a problem to be solved can include the difficulty in aligning a series of derotators on left and right of a spinal column. In particular, when performing various spinal procedures, it is desirable to link together a series of derotators in different thoracic and lumbar zones of the spine so that the derotator series, and the vertebrae to which they are attached, can be rotated in concert to straighten the spinal column. Current derotators have handles that are disposed at a fixed angle relative to a shaft used to reposition the spine, which means that the position of the derotator handles is subject to the anatomy of the patient. This can result in possible positions for the derotators where slots in the handles are not aligned.

The present subject matter can help provide a solution to this problem by providing derotators that include pivotable, variable, articulating, bendable or flexible linkages between the derotator shaft and the derotator handle such that slots in adjacent handles can be more readily aligned with each other. Thus, for example, derotator handles disposed along a left or right side of a spinal column in the superior-inferior direction can be rotated in the anterior-posterior direction to align slots in the handles that receive alignment rods to group the derotators into a series of derotators.

In an example, the present subject matter can help provide a solution to this problem, such as by providing a surgical derotator instrument comprising a shaft, a handle and an articulating coupler. The shaft can comprise a first end portion having a bone anchor coupling and a second end portion opposite the first end portion. The handle can comprise a body portion and a slot extending in the body portion. The articulating coupler can connect the shaft and the handle.

In another example, a surgical instrument can comprise a lever having a first end and a second end, a bone anchor attachment mechanism connected to the lever proximate the first end, an articulating coupler connected to the lever proximate the second end, and a slotted handle connected to the articulating coupler.

In yet another example, a method for coupling a plurality of derotator instruments into a series of derotators can comprise: attaching a plurality of derotator instruments to a plurality of adjacent bone anchors, each derotator instrument comprising: a shaft for connecting to a bone anchor, a handle having a slot, and an adjustable coupler connecting the shaft and the handle; adjusting one or more of the adjustable couplers to align at least one of the slots of the series of derotators with other slots of the series; and inserting an elongate member through the at least one slots that are aligned.

This overview is intended to provide an overview of subject matter of the present patent application. It is not intended to provide an exclusive or exhaustive explanation of the invention. The detailed description is included to provide further information about the present patent application.

DETAILED DESCRIPTION

Figure 1:
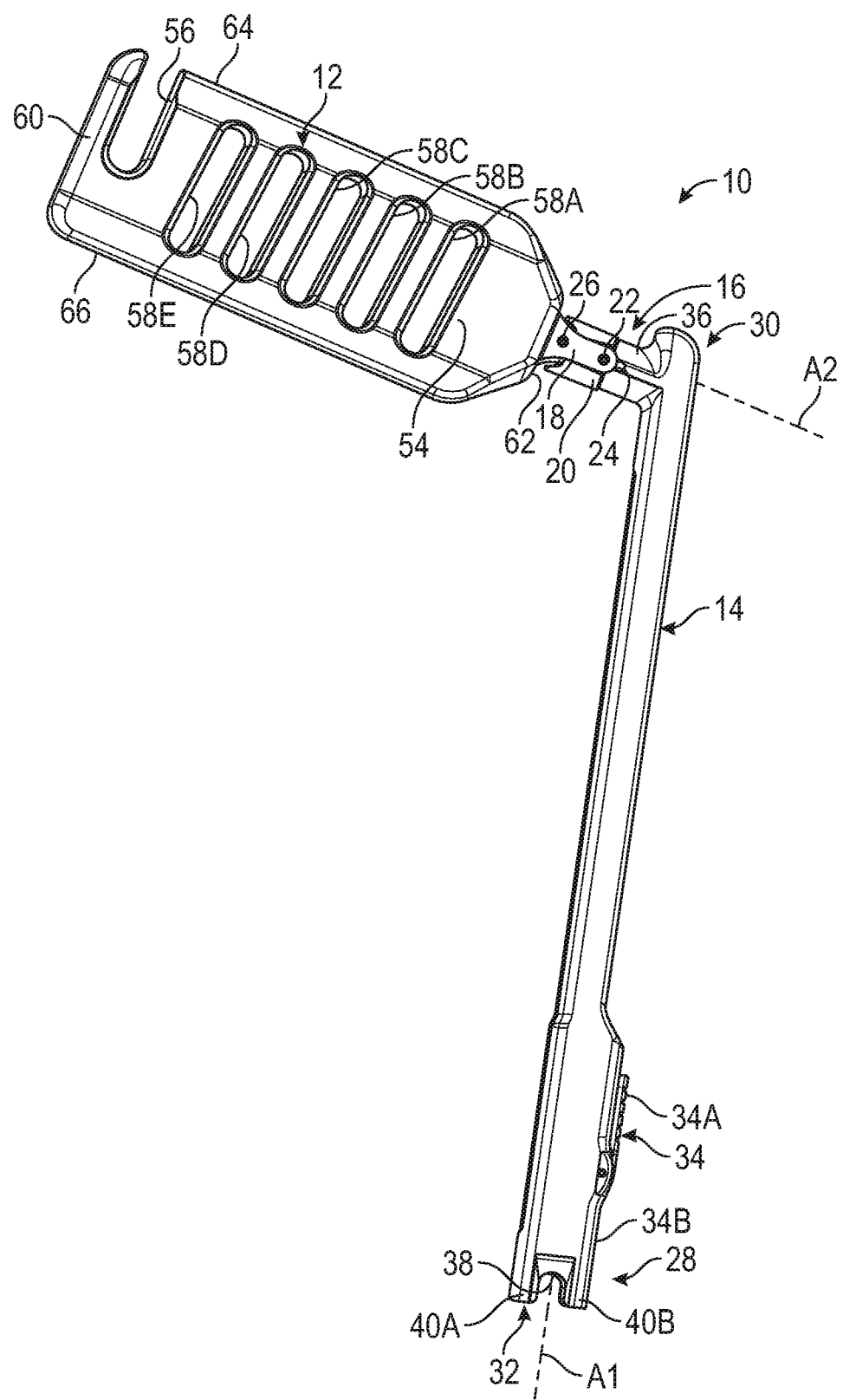
FIG. 1 is a front view of a derotator according to the present disclosure having a handle and a shaft connected by an articulating coupling.
Figure 2:
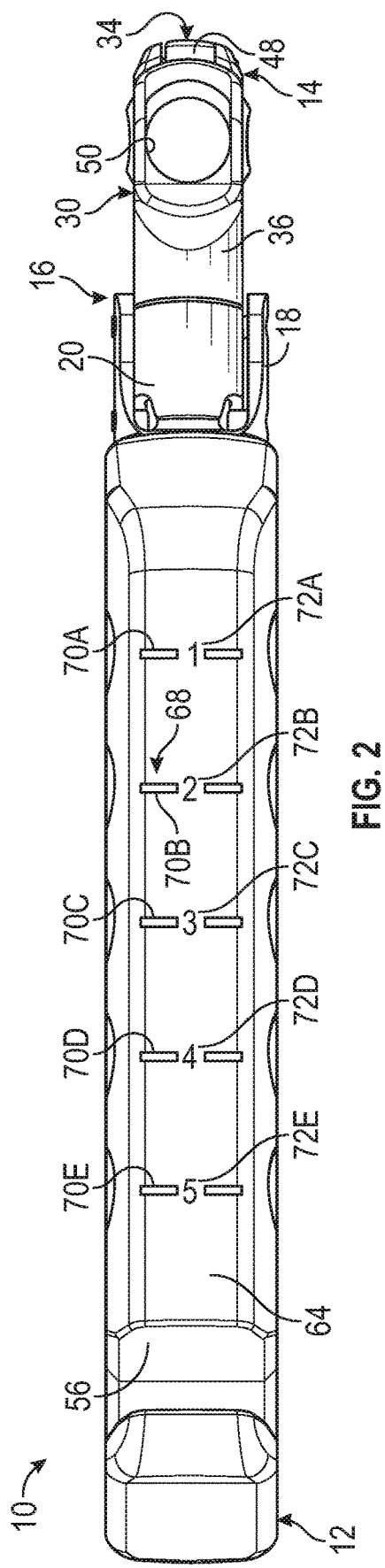
FIG. 2 is a top view of the derotator of FIG. 1 showing indicia on the handle.
Figure 3:
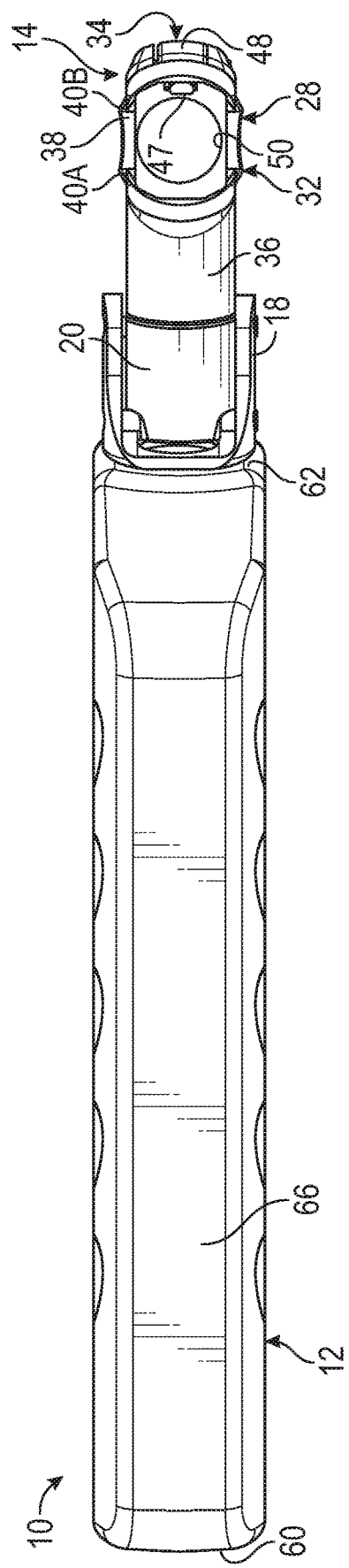
FIG. 3 is a bottom view of the derotator of FIG. 1 showing arms of a handle coupler of the articulating coupling.
Figure 4:
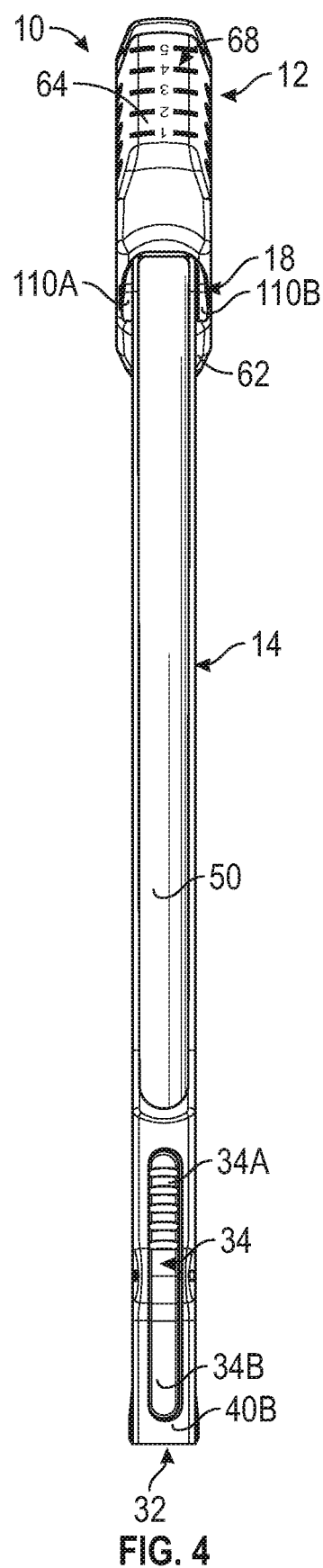
FIG. 4 is a medial side view of the derotator of FIG. 1 showing a bone anchor release mechanism.
Figure 5:
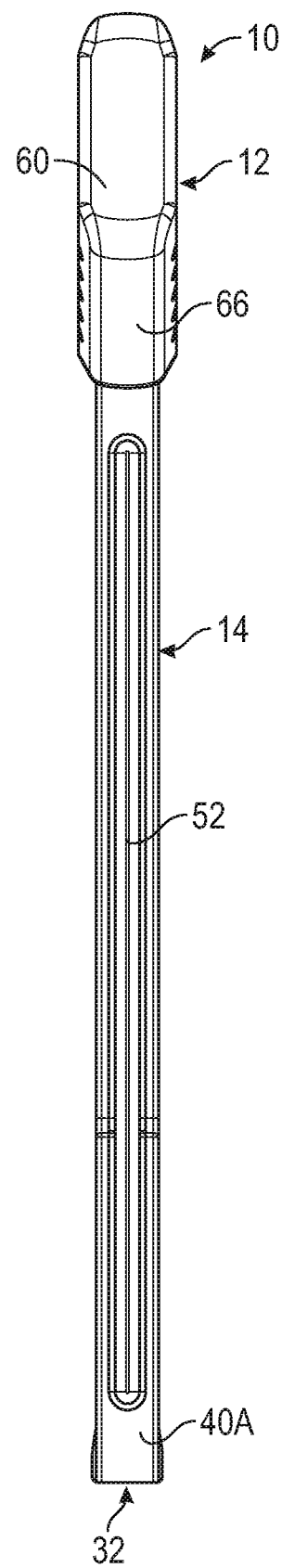
FIG. 5 is a lateral side view of the derotator of FIG. 1 showing a channel extending along the shaft.

FIG. 1 is a front view of derotator 10, which can include handle 12 and shaft 14 connected by articulating coupling 16. Articulating coupling 16 can comprise handle coupler 18 and shaft coupler 20, which can be pivotably connected to each other at pin 22. Shaft coupler 20 can be connected to shaft 14 at pin 24. Handle coupler 18 can be connected to handle 12 via any suitable coupling, such as an interference fit, a pinned connection or a threaded connection. As will be discussed in greater detail below, the angular rotation of handle coupler 18 relative to shaft coupler 20 at pin 22 can be locked into place using pin 26. FIG. 2 is a top view of derotator 10 of FIG. 1. FIG. 3 is a bottom view of derotator 10 of FIG. 1. FIG. 4 is a medial side view of derotator 10 of FIG. 1. FIG. 5 is a lateral side view of derotator 10 of FIG. 1. FIGS. 2-5 are discussed concurrently with FIG. 1.

Figure 6:
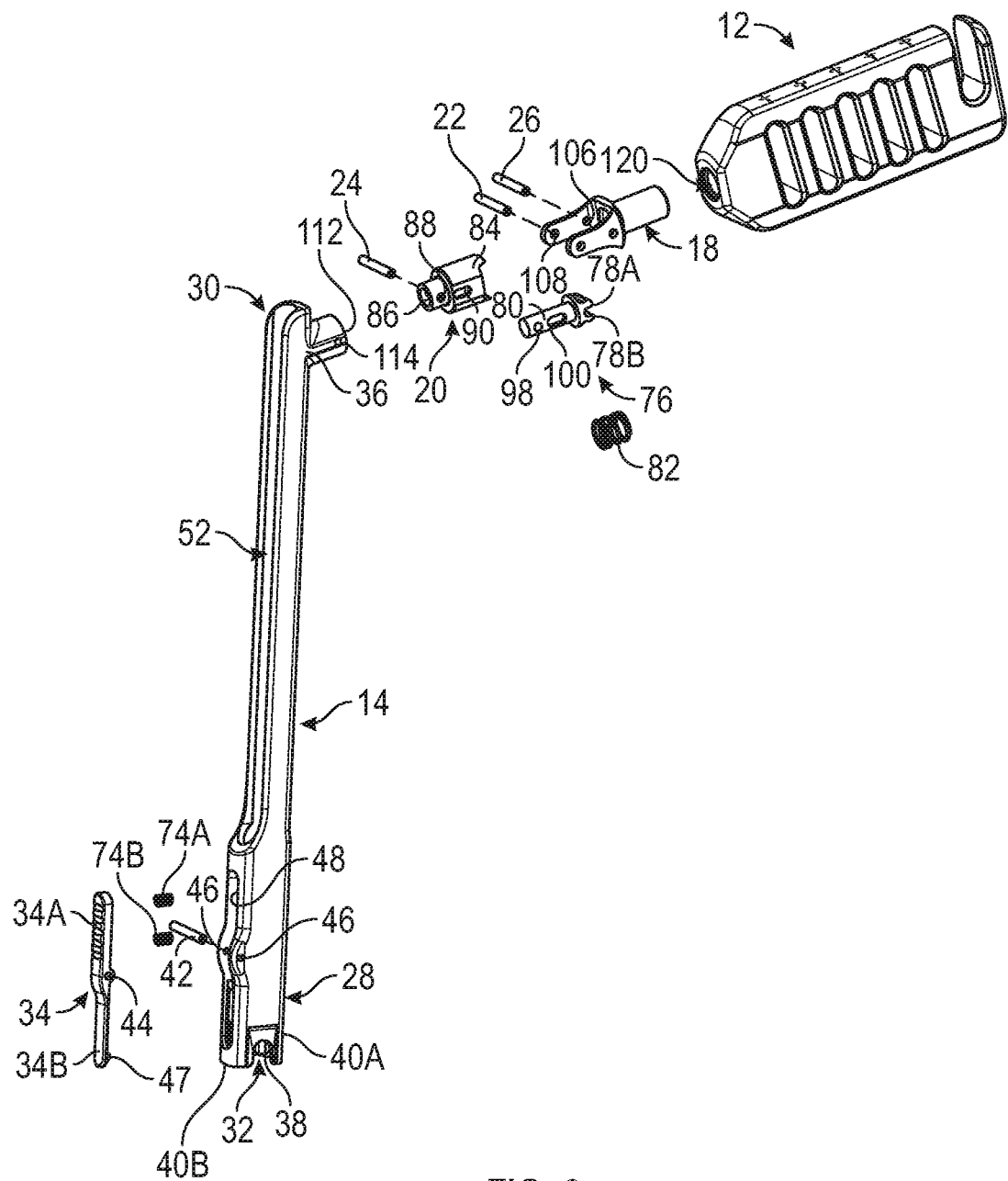
FIG. 6 is an exploded perspective view of the derotator of FIGS. 1-5 showing a shaft coupler and a handle coupler of the articulating coupling.

Shaft 14 can extend from distal end portion 28 to proximal end portion 30. Shaft 14 can be a solid body or a hollow body. For example, shaft 14 can be configured to allow a faster to axially pass through the body of shaft 14. Distal end portion 28 can include anchor coupler 32 and button 34. Proximal end portion 30 can include neck 36. Anchor coupler 32 can comprise a socket that can allow shaft 14 to be coupled to a housing of a bone anchor. For example, coupler 32 can include saddle 38 that allows coupler 32 to fit around a rod extending through the bone anchor housing, while arms 40A and 40B can be configured to extend around the rod to engage the housing. Button 34 can be connected to shaft 14 via pin 42, or some other catch, and can allow button 34 to pivot or rock at pin 42. Specifically, as shown in FIG. 6, button 34 can include pin hole 44 and shaft 14 can include pin hole 46 that receive pin 42.

Button 34 can include proximal end 34A and distal end 34B. Distal end 34B can include an interface feature (e.g., detent 47 of FIG. 3) that can engage a housing of a bone anchor, while proximal end 34A can be biased via springs (e.g., springs 74A and 74B of FIG. 6) that push the interface feature into contact with the housing. Proximal end 34A can be depressed, i.e., advanced toward shaft 14, to compress the springs (e.g., springs 74A and 74B of FIG. 6) and retract the interface feature from the housing, thus releasing shaft 14 from the housing. Examples of bone anchor systems having housing that can be used with coupler 32 are described in U.S. Pat. No. 8,936,624 to Shluzas, U.S. Pat. No. 8,496,685 to Landry et al., and U.S. Pat. No. 9,289,244 to Hestad et al.

As shown in FIGS. 4 and 5, shaft 14 can also include recess 48 (FIG. 3) for button 34 as well as channels 50 and 52 extending from proximate button 34 to proximate neck 36. Channel 52 can lighten shaft 14 and provide stiffening to shaft 14. Channel 50 can extend down past button 34 to allow access to a bone anchor connected to anchor coupler 32. In particular, channel 50 can allow a fastener, including a fastener having a head or a housing, to pass through shaft 14, and allow a driver instrument, such as a screw driver, to be inserted through shaft 14 to reach drive features, such as a hex head or Philips head, of a fastener connected to the bone anchor housing.

Neck 36 can extend from shaft 14 near proximal end 30 to facilitate coupling of handle 12 in an initial orientation. Neck 36 can comprise a hollow body, such as a cylindrical body, that forms socket (e.g., socket 112 of FIG. 6) that can receive shaft coupler 20. Neck 36 can extend from shaft 14 at a fixed angle. Specifically, a central axis A1 extending through shaft 14 can intersect a central axis A2 extending through neck 35. The central axes A1 and A2 can intersect at an obtuse angle, such as approximately one hundred degrees. A central axis of shaft coupler 20 can extend coaxially with the central axis A2 of neck 35. Shaft coupler 20 and neck 35 can be connected with pin 24. A central axis of handle coupler 18 can extend into a socket (e.g., socket 120 of FIG. 6) in handle 12 so that handle coupler 18 can be coaxially aligned with the central axis A2 of neck 35. Handle coupler 18 can be connected to shaft coupler 20 with pin 22.

Handle 12 can comprise body 54, such as a paddle or some other grip, that allows grasping of derotator 10. Handle 12 can comprise open slot 56 and a plurality of closed slots 58A-58E. Body 54 can have a lateral or first end 60, medial or second end 62, proximal side 64 and distal side 66. Proximal side 64 can include indicia 68 that can comprise a plurality of hash marks 70A-70E and identifiers 72A-72E for each of slots 58A-58E. Open slot 56, which can comprise a U-shaped aperture, can extend into proximal side 64. Slots 58A-58E can be disposed between proximal side 64 and distal side 66.

Slots 56 and 58A-58E can be generally elongated between proximal side 64 and distal side 66, and can be spaced along body 54 between lateral end 60 and medial end 62. Although slots 56 and 58A-58E are illustrated as being substantially elliptical elongated slots, the slots can have any shape, such as rectangular, and could be positioned in any desired orientation. Further, although multiple slots are described and illustrated herein, handle 12 can include a single slot. Slots 58A-58E can receive a device, such as an elongate member, a pin or a rod, to couple derotator 10 to other derotator instruments in series of derotators. Slot 56 can be used in conjunction with a flexible elongate strap of material, such as a loop of gauze, to allow a surgeon or practitioner to more easily manipulate derotator 10.

Suitable rotation instruments in which articulating coupling 16 can be used include those described herein, and those commercially available from Zimmer Biomet Spine, Inc. of Broomfield, Colo., such as those used as part of the Trivium™ Derotation System. By coupling derotator 10 to one or more adjacent rotation instruments, multiple vertebral bodies can be rotated substantially simultaneously to enable correction across multiple levels in a spinal column, as will be discussed in greater detail with reference to FIGS. 11A-11D.

Figure 7:
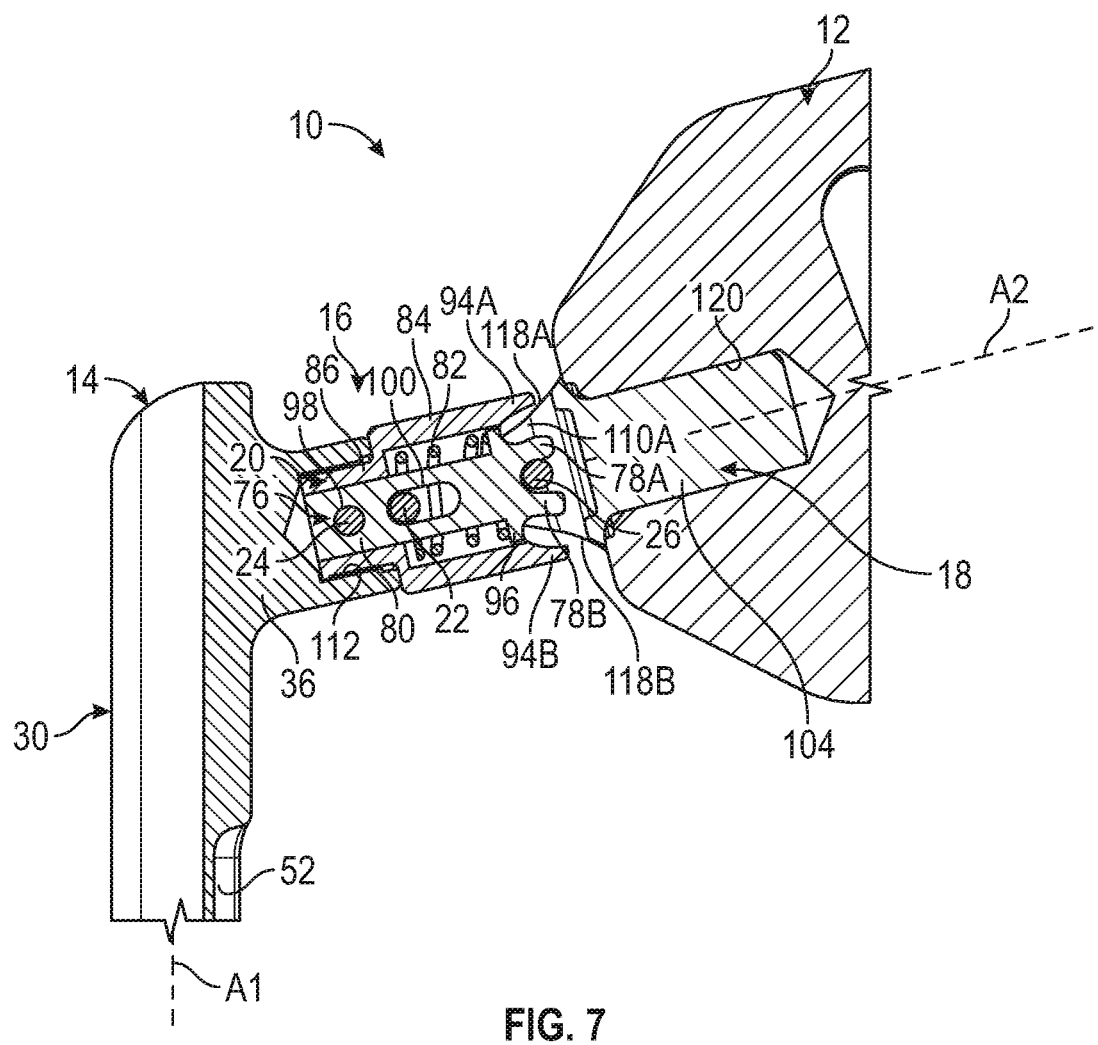
FIG. 7 is a cross-sectional view of the articulating coupling of FIGS. 1-5 showing an angled lock and a spring positioned between the shaft coupler and the handle coupler.
Figure 8:
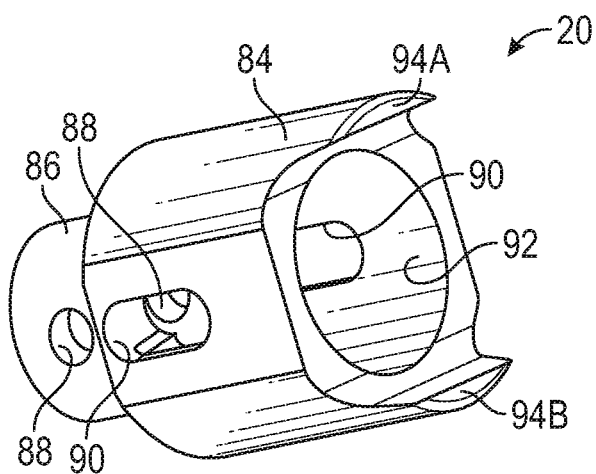
FIG. 8 is a perspective view of the shaft coupler of FIGS. 6 and 7.
Figure 9:
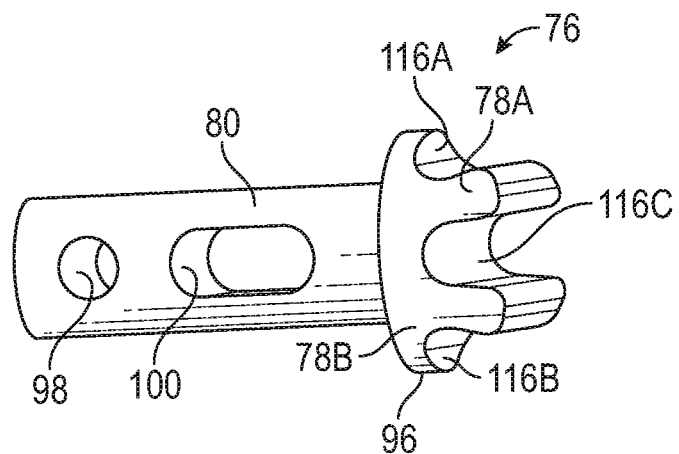
FIG. 9 is a perspective view of the angled lock of FIGS. 6 and 7.
Figure 10:
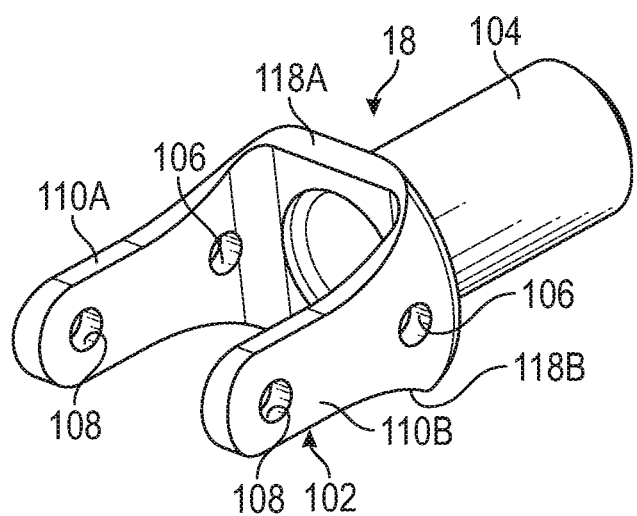
FIG. 10 is a perspective view of the handle coupler of FIGS. 6 and 7.

FIG. 6 is an exploded perspective view of derotator 10 of FIGS. 1-5 showing handle coupler 18 and shaft coupler 20 of articulating coupling 16. FIG. 7 is a cross-sectional view of articulating coupling 16 of FIGS. 1-6 showing angled lock 76 positioned between handle and shaft couplers 18 and 20. FIG. 8 is a perspective view of shaft coupler 20 of FIGS. 6 and 7. FIG. 9 is a perspective view of angled lock 73 of FIGS. 6 and 7. FIG. 10 is a perspective view of handle coupler 18 of FIGS. 6 and 7. FIGS. 7-10 are discussed concurrently with FIG. 6.

As shown in FIG. 6, distal end 34B of button 34 can include detent 47 that can engage a housing of a bone anchor, while proximal end 34A can be biased via springs 74A and 74B that push the interface feature into contact with the housing. Proximal end 34A can be depressed, i.e., advanced toward shaft 14 to compress springs 74A and 74B and retract the interface feature from the housing, thus releasing shaft 14 from the housing.

As shown in FIG. 6, angled lock 76 can be positioned coaxially between handle coupler 18 and shaft coupler 20. Angled lock 76 can include teeth 78A and 78B and stem 80. Spring 82 can be positioned around stem 80. As can best be seen in FIG. 8, shaft coupler 20 can include collar 84, post 86, pin hole 88, aperture or slot 90, socket 92 and flanges 94A and 94B. As can best be seen in FIG. 9, angled lock 76 can include teeth 78A and 78B, stem 80, disk 96, pin hole 98 and aperture or slot 100. As can best be seen in FIG. 10, handle coupler 18 can include yoke 102, post 104, pin hole 106 and pin hole 108. Yoke 102 can include flanges 110A and 110B. The components of derotator 10 can be made or fabricated from any suitable material, such as various medical grade metals and plastics. In an example, handle 12 can be made of polyphenylsulfone (i.e., Radel®) and shaft 14 can be made of a stainless steel.

Spring 82 can be positioned around stem 80 of angled lock 76 to bias handle coupler 18 toward angled lock 76. Teeth 78A and 78B can be angled relative to a central axis of stem 80 extending along axis A2 and to align with flanges 94A and 94B of shaft coupler 20. Teeth 78A and 78B can engage pin 26 to lock articulating coupling 16 into a plurality of discrete angular positions that position handle 12 into a plurality of discrete angular positions relative to shaft 14. In particular, articulating coupling 16 can be configured to connect handle 12 and shaft 14 so that handle and shaft 14 can pivot relative to each other in only one plane. In the example embodiment of the present application, articulating coupling 16 can be configured to allow handle 12 and shaft 14 to pivot in a plane extending through both handle 12 and shaft 14, that is, a plane extending through the central axis of shaft 14 (e.g., axis A1) and the central axis of handle 12 (e.g., axis A2) extending centrally through articulating coupling 16.

Post 86 of shaft coupler 20 can be inserted into socket 112 of neck 36 on shaft 14. Post 86 can include pin hole 88 that can align with pin hole 114 on neck 36. Pin 24 can be inserted into pin hole 114 and pin hole 88 to secure shaft coupler 20 to shaft 14. In other examples, post 86 can be coupled to neck 36 via other means, such as threaded coupling, press fit or interference fit. Collar 84 can extend coaxially from post 86 and can include socket 92 for receiving stem 80 of angled lock 76. Spring 82 can be positioned around stem 80 before stem 80 is inserted into socket 92 of collar 84. Stem 80 can include pin hole 98 for aligning with pin holes 88 and 114 to immobilize angled lock 76 within shaft coupler 20. Slot 100 of angled lock 76 can align with slot 90 in shaft coupler 20. Pin hole 108 of handle coupler 18 can align with slot 100 and slot 90. Pin 22 can be inserted into pin hole 108 and slots 90 and 100. Spring 82 can be positioned between pin 22 and disk 96 of angled lock 76. As such, flanges 110A and 110B (FIG. 10) of handle coupler 18 can be translated alongside collar 84 of shaft coupler 20 to compress spring 82 as pin 22 pushes spring 82 against disk 96. Handle coupler 18 can be pivoted on pin 22 such that pin hole 106 can be positioned to align with the spaces alongside and in between teeth 78A and 78B that define slots 116A, 116B and 116C (FIG. 9). Pin 26 can be inserted into pin hole 106 and, depending on the rotational position of handle coupler 18, can be located above tooth 78A, between teeth 78A and 78B, or below tooth 78B (with reference to the orientation of FIGS. 6 and 7) so as to be disposed in slot 116A, slot 116C or slot 116B, respectively. Post 104 of handle coupler 18 can be inserted into socket 120 in handle 12. Post 104 can be coupled to socket 120 via any suitable means, such as pinned coupling, threaded coupling, press fit or interference fit. Pins 22, 24 and 26 can be held in place in their respective pin holes via press fit, or by any other suitable means, such as threading or interference fit. Additionally, although articulating coupling 16 has been described as including pins 22, 24 and 26, articulating coupling 16 can include other types of catch mechanism, such as flanges, rods, elongate members, stakes, shafts and the like.

During operation, with specific reference to FIG. 7, shaft coupler 20 and angled lock 76 can be anchored to neck 36 via pin 24 extending through pin holes 114 and 88. Pin 22 can be inserted into slots 90 and 100 such that a center portion of pin 22 is located in slots 90 and 100, and end portions of pin 22 are located in flanges 110A and 110B of yoke 102 of handle coupler 18 in pin hole 108. Thus, pin 22 can be pulled by flanges 110A and 110B (such as by someone pulling handle 12 away from neck 36) so that pin 22 translates in slots 90 and 100. Spring 82 can thus be pushed by pin 22 against disk 96. Additionally, pin 26 can be moved out of the location between teeth 78A and 78B. Handle 12 can be rotated to cause handle coupler 18 to rotate at pin 22 while handle coupler 18 is pulled away from shaft coupler 20, thereby allowing pin 26 to be repositioned above tooth 78A or below tooth 78B. Handle 12 can be released such that spring 82 pushes handle coupler 18 back towards shaft coupler 20 via pin 22. Flanges 94A and 94B can be sized and positioned to limit rotation of handle coupler 18. In particular, when shoulder 118A of yoke 102 engages flange 94A, pin 26 will align with socket 116A, and when shoulder 118B of yoke 102 engages flange 94B, pin 26 will align with socket 116B.

As such, the angular position of handle 12, such as can be determined via a central axis extending through post 104 (e.g., axis A2), relative to a central axis of shaft 14 (e.g., axis A1), can be changed into one of three discrete positions determined by teeth 78A and 78B. In other examples, an angled lock can have additional or fewer teeth to provide a different number of discrete positions. In the example described, articulating coupling 16 is configured to restrict movement of handle 12 to within only the plane defined by axis A1 and axis A2.

Figure 11A:
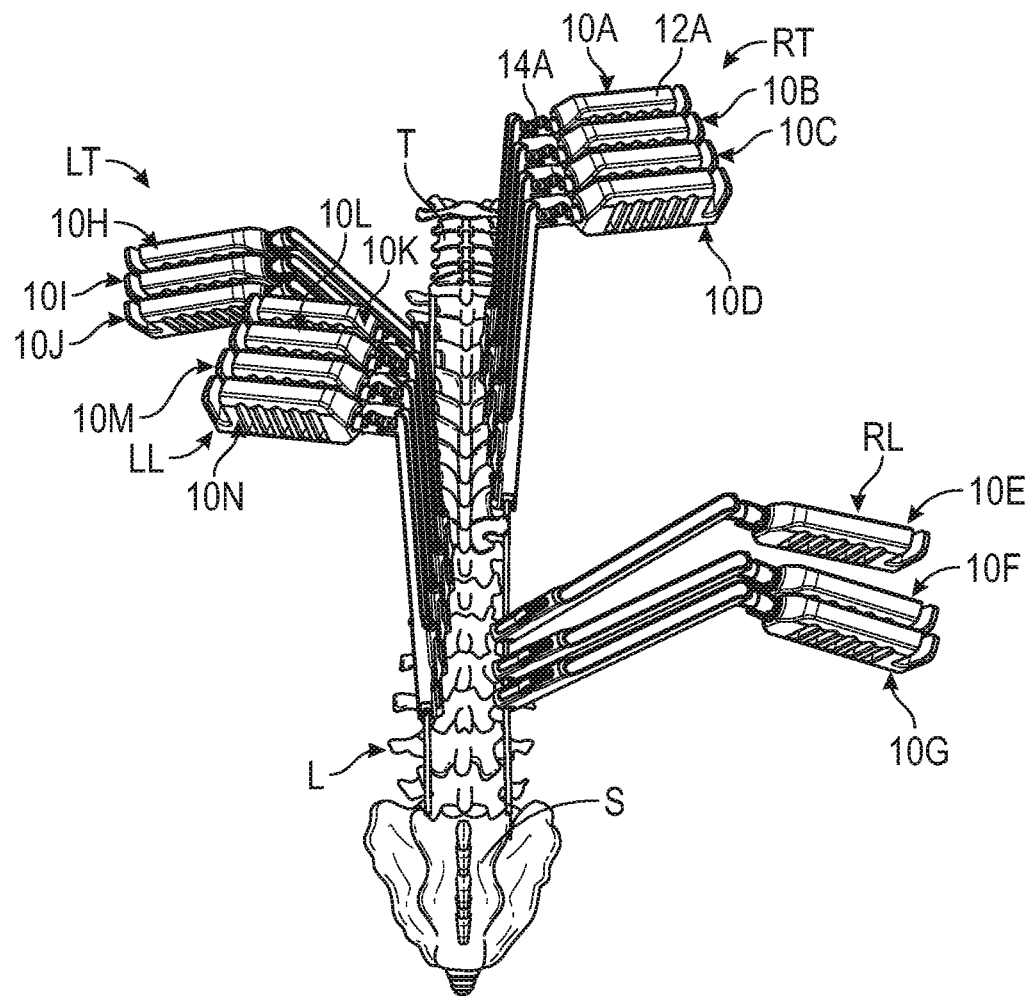
FIG. 11A is a perspective view of a plurality of derotators of the present application connected to a plurality of bone anchors attached to an un-straightened spine.

FIG. 11A is a perspective view of a plurality of derotators 10A-10N of the present application connected to a plurality of bone anchors 130 attached to an un-straightened spine S. Although the bone anchors to which derotators 10A-10N of are connected cannot be seen in FIGS. 11A-11D, bone anchors 130 shown in FIGS. 11C and 11D are representative of bone anchors having housings and fasteners described herein that can be attached to couplers 32 of derotators 10.

Fasteners of bone anchors 130 can be connected to pedicles of spine S along medial and lateral sides of spine S in thoracic zone T and lumbar zone L of spine S.

Figure 11B:
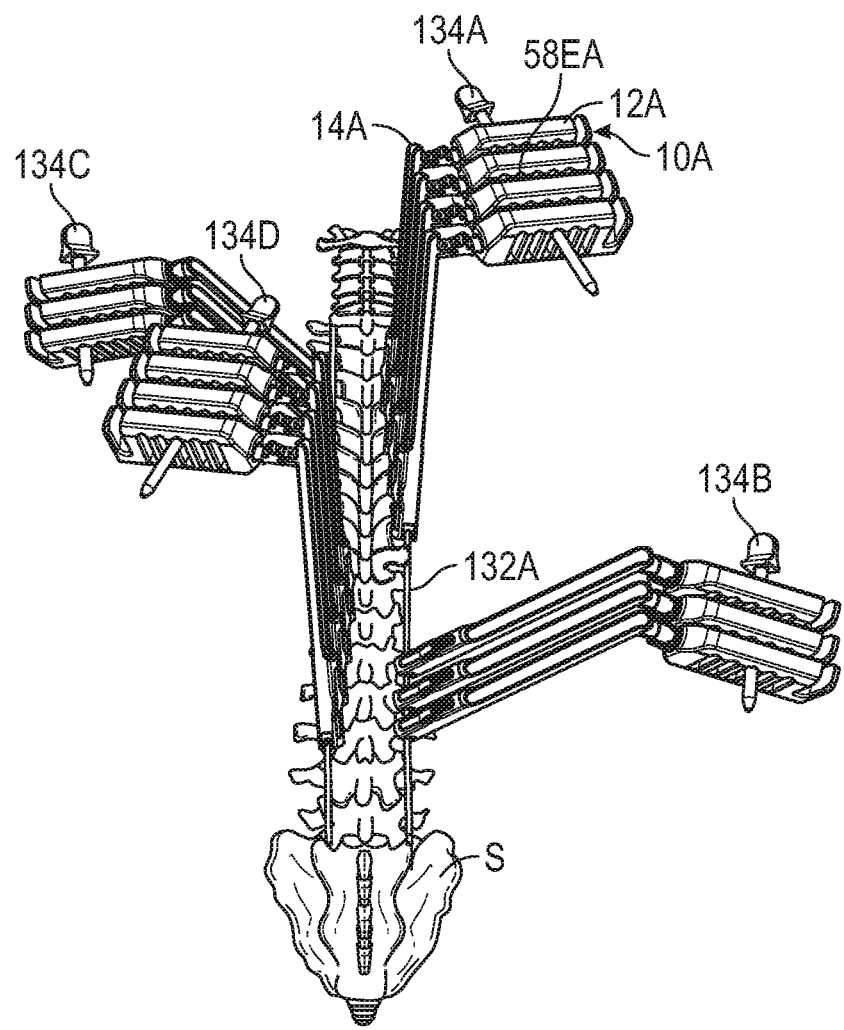
FIG. 11B is a perspective view of the plurality of derotators of FIG. 11A wherein handle linkage rods are inserted into left and right lumbar and thoracic series of the derotators.
Figure 11C:
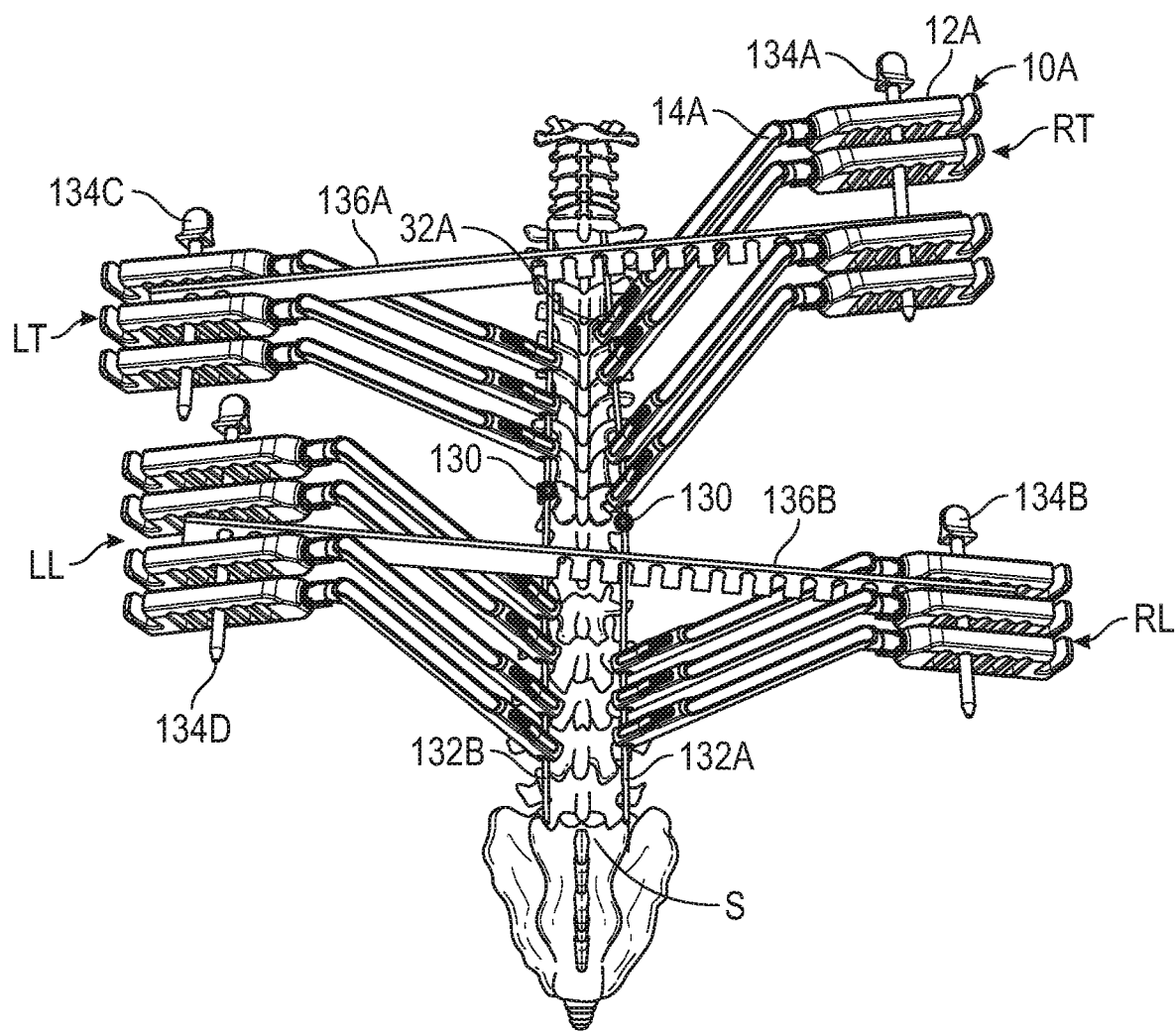
FIG. 11C is a perspective view of the plurality of derotators of FIG. 11B wherein the left and right derotator series are connected by combs for each of the lumbar and thoracic series.
Figure 11D:
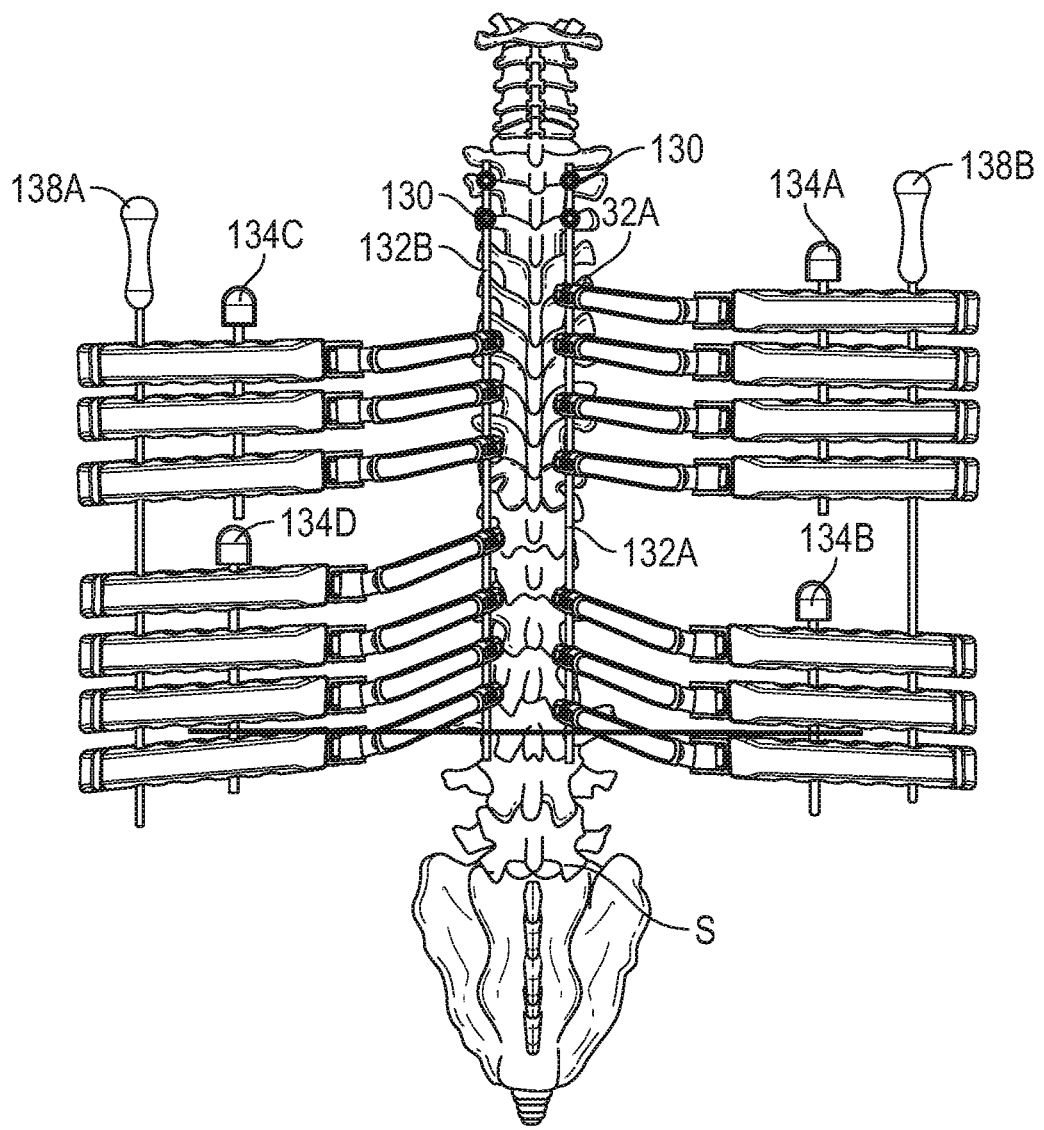
FIG. 11D is a top view of the plurality of derotators of FIG. 11C wherein series alignment rods are inserted into the left lumbar and thoracic series and the right lumbar and thoracic series after the spine has been straightened.

Each fastener can have a housing that can receive one of rods 132A and 132B (FIGS. 11C and 11D). Each shaft 14 of derotators 10A-10N can include a coupler 32 that can attach to one of the anchor housings while a rod is inserted in the housing. Each shaft 14 is attached to a handle 12 in a rotatable manner, such as by using an articulating coupling 16 described herein. Only derotator 10A is shown with reference numbers for handle 12A, shaft 14A, coupler 32A (FIG. 11D) and slot 58EA (FIG. 11B) for clarity.

Derotators 10A-10N can be grouped into four discrete series of derotators. In particular, derotators 10A-10D can be grouped in a right-side thoracic series RT, derotators 10E-10G are grouped in a right-side lumbar series RL, derotators 10H-10J are grouped in a left-side thoracic series LT, and derotators 10K-10N are grouped in a left-side lumbar series LL. As can be seen in FIG. 11A, the derotators in each series are not substantially aligned with each other such that slots 58A-58E within each handle 12 are not aligned with each other. As such, it can be difficult for a surgeon or practitioner to insert alignment devices, such as elongate members, into slots 58A-58E without the burden of aligning each individual derotator, which can sometimes require difficult maneuvering of spine S. As such, derotators 10A-10N of the present disclosure allow for handles 12 to be rotated relative to shafts 14 so that slots 58A-58E in adjacent derotators can be more easily aligned with each other.

FIG. 11B is a perspective view of the plurality of derotators 10A-10N of FIG. 11A wherein handle linkage rods 134A-134D are inserted into left and right lumbar and thoracic series RT, LT, RL and LL of the derotators 10A-10N. As such, the derotators in each series are linked to each other and can be rotated in unison to perform a straightening procedure on spine S, as is briefly discussed with reference to FIGS. 11C and 11D. Handle linkage rods 134A-134D can comprise elongate members capable of being inserted through a plurality of slots in a plurality of aligned derotators. The elongate members can include various rigid or semi-rigid bodies for linking the derotators. For example, handle linkage rods 134A-134D can comprise pins, rods, bars, dowels, bars, stakes and the like. The elongate members can have different cross-sectional areas, such as circular, rectangular, square, rectilinear, or the like, and the cross-sectional areas need not be uniform along the length of the elongate members. The elongate members can include handles to facilitate insertion by a surgeon and to assist in preventing the elongate members from being withdrawn from the slots.

FIG. 11C is a perspective view of the plurality of derotators 10A-10N of FIG. 11B wherein the thoracic derotator series LT and RT are connected by comb 136A and the lumbar derotator series LL and RL are connected by comb 136B. Combs 136A and 136B can include teeth that form slots for connecting to handle linkage rods 134A-134D. Combs 136A and 136B permit the thoracic zone T and lumbar zone L of spine S to be rotated by applying force to each side of the zone at the same time, respectively. Comb 136A links series LT and RT so that force can be applied to the left and right side of each vertebra at the left and right side pedicles, thereby reducing stress on each pedicle in the thoracic zone T. Comb 136B links series LL and RL so that force can be applied to the left and right side of each vertebra at the left and right side pedicles, thereby reducing stress on each pedicle in the lumbar zone L. With the thoracic series LT and RT and lumbar series LL and RL connected, force can be applied to spine S via derotators 10A-10N to rotate spine S into alignment. Shafts 14 of derotators 10A-10N act as lever arms for increasing force applied to handles 12, thereby increasing the ability of the surgeon or practitioner to rotate the spinal column. For example, series LT and RT can be rotated clockwise and series LL and RL can be rotated counter-clockwise to align the individual vertebra of spine S.

FIG. 11D is a top view of the plurality of derotators 10A-10N of FIG. 11C wherein series alignment rods 138A and 138B are inserted into the left lumbar and thoracic series and the right lumbar and thoracic series, respectively, after the spine S has been straightened. Combs 136A and 136B can be removed from derotators 10A-10N and series alignment rods 138A and 138B can be inserted into slots 58A-58E of handles 12. Series alignment rots 138A and 138B can permit spine S to be readily held in place so that subsequent surgical procedures can be performed on spine S.

Series alignment rods 138A and 138B can comprise elongate members capable of being inserted through a plurality of slots in a plurality of aligned derotators in a plurality of aligned series of derotators. The elongate members can include various rigid or semi-rigid bodies for linking the derotators. For example, series alignment rods 138A and 138B can comprise pins, rods, bars, dowels, bars, stakes and the like. The elongate members can have different cross-sectional areas, such as circular, rectangular, square, rectilinear, or the like, and the cross-sectional areas need not be uniform along the length of the elongate members. The elongate members can include handles to facilitate insertion by a surgeon and to assist in preventing the elongate members from being withdrawn from the slots.

Figure 12:
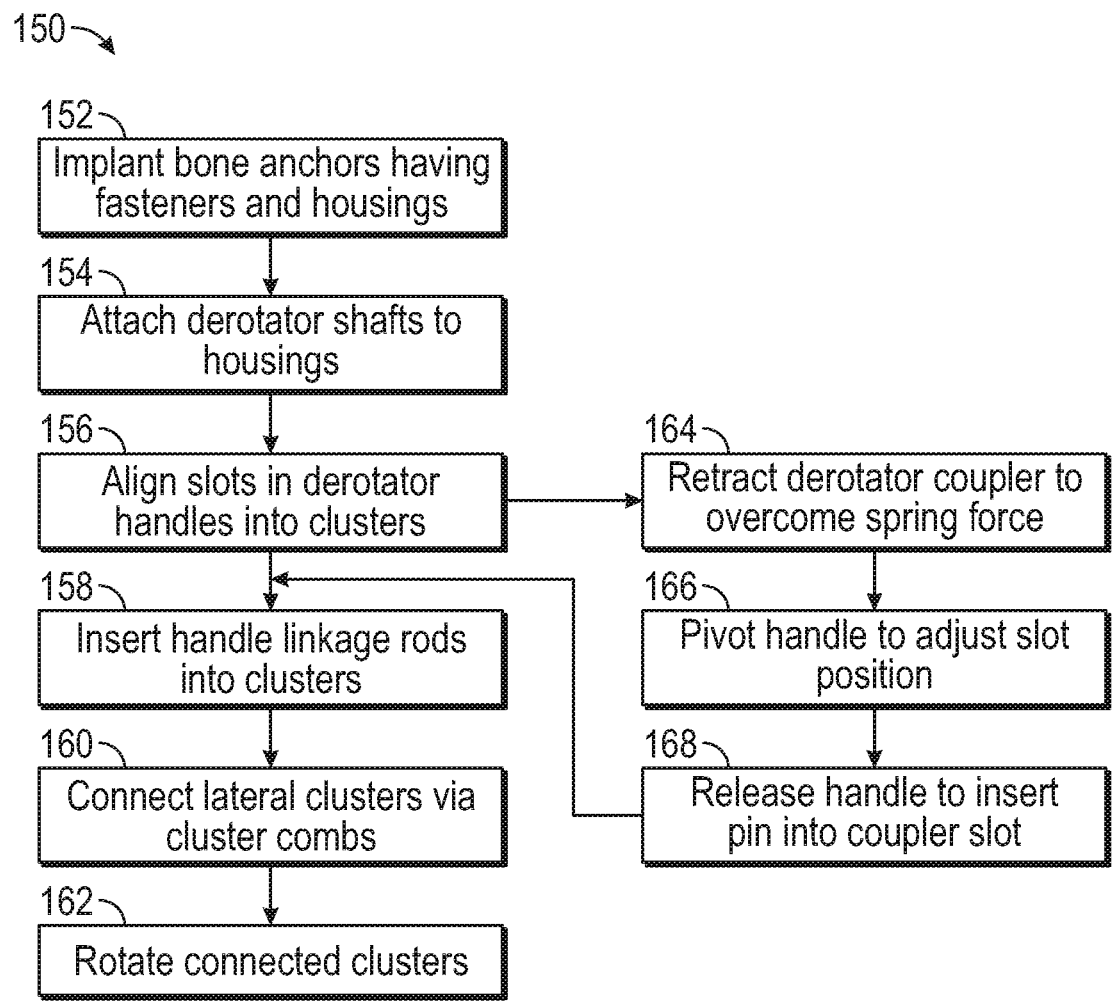
FIG. 12 is a flow chart diagramming a method for coupling a plurality of derotator instruments described herein into a series for simultaneous rotation.

FIG. 12 is a flow chart diagramming method 150 for coupling a plurality of derotator instruments, such as derotator 10, described herein into a series of derotators for simultaneous rotation. Method 150 can include step 152 of implanting bone anchors having fasteners and housings, step 154 of attaching derotator shafts to the anchor housings, step 156 of aligning slots in derotator handles into series, step 158 of inserting handle linkage rods into the aligned slots of the series, step 160 of connecting lateral series of derotators via series combs, and step 162 of rotating the connected series of derotators.

Step 156 can include sub-steps comprising step 164 of retracting a derotator coupler component to overcome spring force in a articulating coupler, step 166 of pivoting a handle of a derotator to adjust slot position, and step 168 of releasing the handle of the derotator to insert a catch or pin of the articulating coupler into a coupler slot.

Step 152 can comprise implanting a plurality of bone anchors, such as bone anchors 130 of FIG. 11C, into a spinal column. In particular, fasteners, such as threaded fasteners of the bone anchors can be threaded into pedicles of the spinal column. Each bone anchor can have a housing attached to the faster that can connect to a stabilization rod. A stabilization rod, such as rods 132A and 132B of FIG. 11C, can be inserted into a plurality of bone anchor housings disposed along one side (i.e., left or right side) of the spinal column. Typically, one rod is implanted along each of the left and right sides. The left and right rods can be shaped, e.g., bent, to accommodate curvature of the spine and to fit the rods into the housings.

Step 154 can comprise attaching shafts 14 of derotators 10 to a plurality of the bone anchor housings. In particular, couplers 32 can be used to attach to the housing of the bone anchors. Derotators 10 can be attached in series, as described above.

Step 156 can comprise aligning slots 58A-58E in handles 12 of derotators 10. In particular, a single one of slots 58A-58E in each handle of a series can be aligned to receive an elongate member, such as handle linkage rods 134A-134D. As such, it is possible for a rod to extend through slot 58C in one handle 12 and slots 58B and 58D in adjacent handles. Articulating couplings 16 allows the handles 12 to be rotated with respect to their respective shaft 14 to allow for alignment of the various slots 58A-58E without having to move shafts 14 or the vertebrae connected to shafts 14. The example articulating coupling 16 described herein allows for handles 12 and shafts 14 to have only one degree of freedom of movement between each other, e.g., in the plane extending through axes A1 and A2. However, in other examples, multiple degrees of freedom of movement can be provided by articulating coupling 16. Also, other types of movement can be permitted, such as rotation along axis A2, pivoting out of the plane of axes A1 and A2, etc. Although articulating coupling 16 has been described with reference to two coupling components pivoting, such as on a pin, other types of actuation means can be used, such as flexing, bending or rotating and the like. Also, in other examples, a separate coupling component need not be used to couple handle 12 and shaft 14 such that handle 12 can be directly connected to shaft 14. For example, handle coupler 18 could be made integral with body 54 and could be directly pinned or coupled to shaft 14 at a pivot point.

Step 158 can comprise inserting one of handle linkage rods 134A-134D into each of the derotator series described above.

Step 160 can comprise connecting or linking lateral series, such as left-side thoracic series LT and right-side thoracic series RT, and left-side lumbar series LL and right-side lumbar series RL, via series combs 136A and 136B, respectively.

Step 162 can comprise rotating the linked lateral series to straighten the spinal column. For example, left-side thoracic series LT and right-side thoracic series RT can be rotated using comb 136A in one direction, while left-side lumbar series LL and right-side lumbar series RL can be rotated using comb 136B in an opposite direction to straighten the spinal column. Force can be applied to handles 12 connected together in series via handle linkage rods 134A-134D and combs 136A and 136B to rotate the linked series. Shafts 14 of derotators 10 act as lever arms to gain a mechanical advantage in rotating the spinal column. Once rotated, series alignment rods 138A and 138B can be inserted into the straightened series of handles 12 to link all of the employed derotators 10 into a position where the spinal column is in a straightened state. As such, subsequent medical or operation procedures can be carried out. For example, the straightening of the spinal column in step 162 can also deform stabilization rods 132A and 132B so that the spinal column will remain in a straightened state when derotators 10 are removed. After removal of derotators 10, tissue surrounding the spinal column can be repaired or sutured to close-up the incisions surrounding the spinal column.

Step 164 can comprise pulling on handle 12 to retract handle coupler 18 away from shaft coupler 20. In so doing, spring 82 can be compressed between pin 22 and disk 96 of angled lock 76. As such, pin 26 can be retracted from being within one of slots 116A-116C.

Step 166 can comprise pivoting handle 12 of derotator 10 to adjust the position of pin 26 to the location of one of slots 116A-116C. With pin 26 removed from engagement with angled lock 76, handle 12 and handle coupler 18 can be rotated on pin 22 to, for example, move pin 26 over slot 116A.

Step 168 can comprise releasing handle 12 of derotator 10 to position pin 26 into one of slots 116A-116C, such as slot 116A. Spring 82 can push against pin 22 to move pin 26 into the desired slot. Spring 82 holds pin 26 in the desired slot so that handle 12 cannot accidentally slip out of the desired slot during a procedure. Likewise, teeth 78A and 78B that form slots 116A-116C hold pin 26 in one of a plurality of discrete positions such that handle 12 does not freely pivot during a procedure. Flanges 94A and 94B and shoulders 118A and 118B facilitate rotation of handle 12 into positions where pin 26 will readily align with slots 116A and 116B, respectively.

Figure 13:
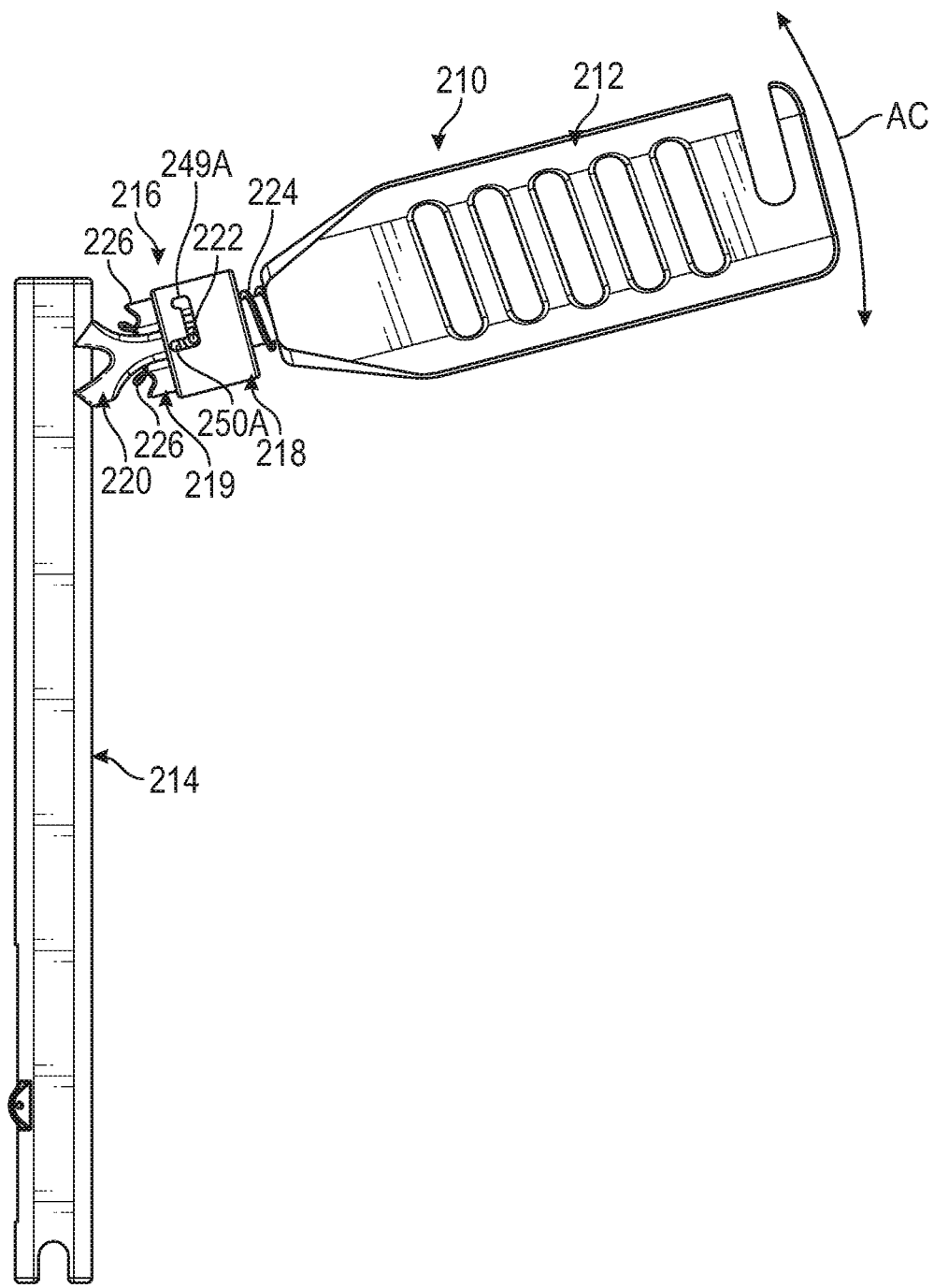
FIG. 13 is a front view of a derotator according to the present disclosure having a handle and shaft connected by an articulating coupling having a locking collar.
Figure 14:
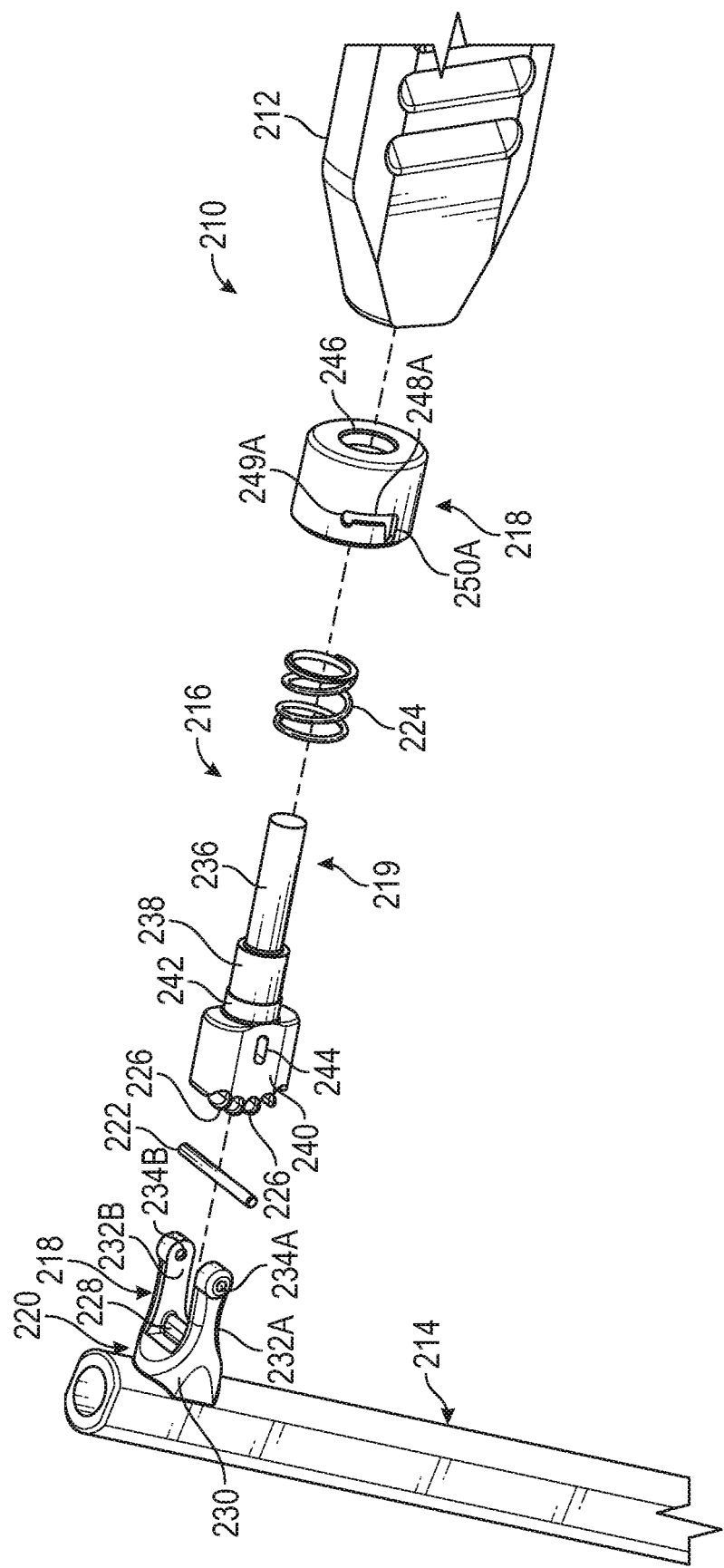
FIG. 14 is an exploded perspective view of the derotator of FIG. 13 showing a spring disposed between a handle coupler and the locking collar.

FIG. 13 is a front view of derotator 210 according to the present disclosure having handle 212 and shaft 214 connected by articulating coupling 216 having locking collar 218. Articulating coupling 216 can also comprise handle coupler 219 and shaft coupler 220, which can be pivotably connected to each other at pin 222. Locking collar 218 can also be coupled to pin 222 and spring 224 can be captured between locking collar 218 and handle coupler 219. FIG. 14 is an exploded perspective view of derotator 210 of FIG. 13 showing spring 224 disposed between handle coupler 219 and locking collar 218. FIGS. 13 and 14 are discussed concurrently.

Figure 15A:
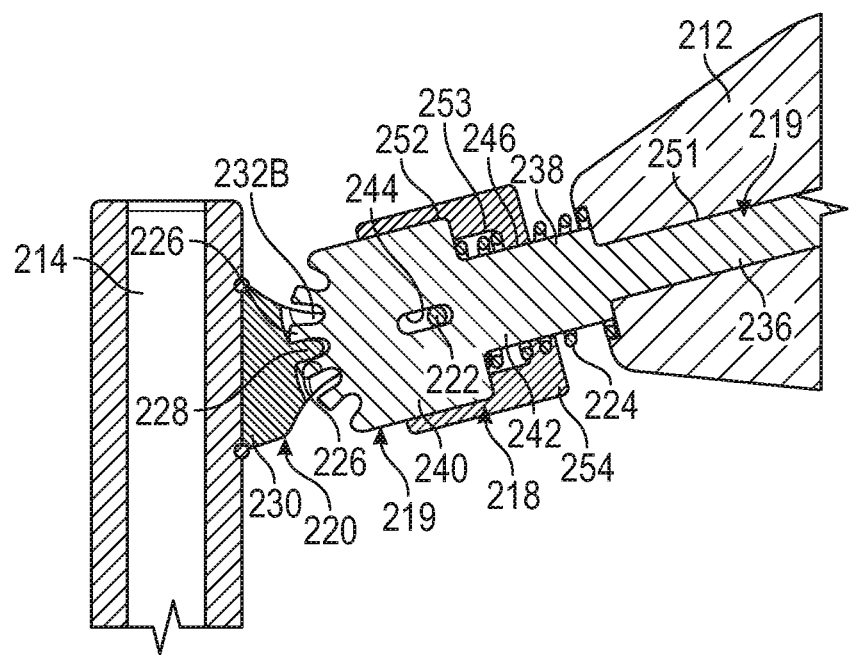
FIG. 15A is a cross-sectional view of the derotator of FIG. 13 showing the locking collar in a position to prevent movement of the handle relative to the shaft.
Figure 15B:
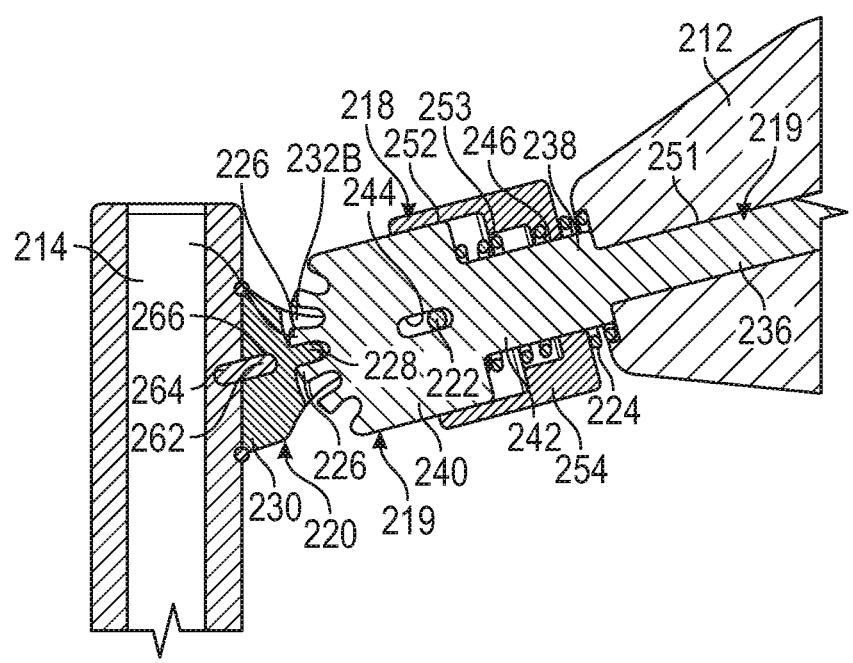
FIG. 15B is a cross-sectional view of the derotator of FIG. 13 showing the locking collar in a position to allow movement of the handle relative to the shaft.

Pin 222 can permit handle coupler 219 pivot relative to shaft coupler 220. As such, handle 212 can move about arc Ac relative to shaft 214. Fingers 226 of handle coupler 219 can engage shelf 228 (FIG. 14) on shaft coupler 220 to lock handle 212 into a plurality of specific angular positions along arc Ac. In the illustrated example, handle coupler 219 can include six fingers 226 that form five locking positions. Spring 224 can push against collar 218 to push handle coupler 219 toward shaft coupler 220 to maintain fingers 226 engaged with shelf 228. Collar 218 can be rotated into two positions that alternatively permit handle coupler 219 to be pulled away from shaft coupler 220 (to the right in FIGS. 13 and 14) to adjust the angle of handle 212 or prevent handle coupler 219 from being pulled away from shaft coupler 220, as is shown in FIGS. 15B and 15A, respectively.

As can be seen in FIG. 14, shaft coupler 220 can include base 230 for attaching to shaft 214 and prongs 232A and 232B that extend from base 230 to receive pin 222. Shelf 228 can extend from base 230 between prongs 232A and 232B. Prongs 232A and 232B can include bores 234A and 234B, respectively, that can receive pin 222.

Handle coupler 219 can include shaft portion 236, slide portion 238 and pivot portion 240. Slide portion 238 can include land 242 for receiving spring 224. Pivot portion 240 can include slot 244 for receiving pin 222. Fingers 226 can extend from pivot portion 240 in the opposite direction as slide portion 238 and shaft portion 236.

Locking collar 218 can include shaft bore 246 for receiving shaft portion 236 and pin slots 248A and 248B (FIGS. 18 and 19) for receiving pin 222. Slots 248A and 248B can include short ends 249A and 249B and long ends 250A and 250B. Handle 212 can include coupling bore 251 (FIGS. 15A and 15B) for receiving shaft portion 236.

Figure 18:
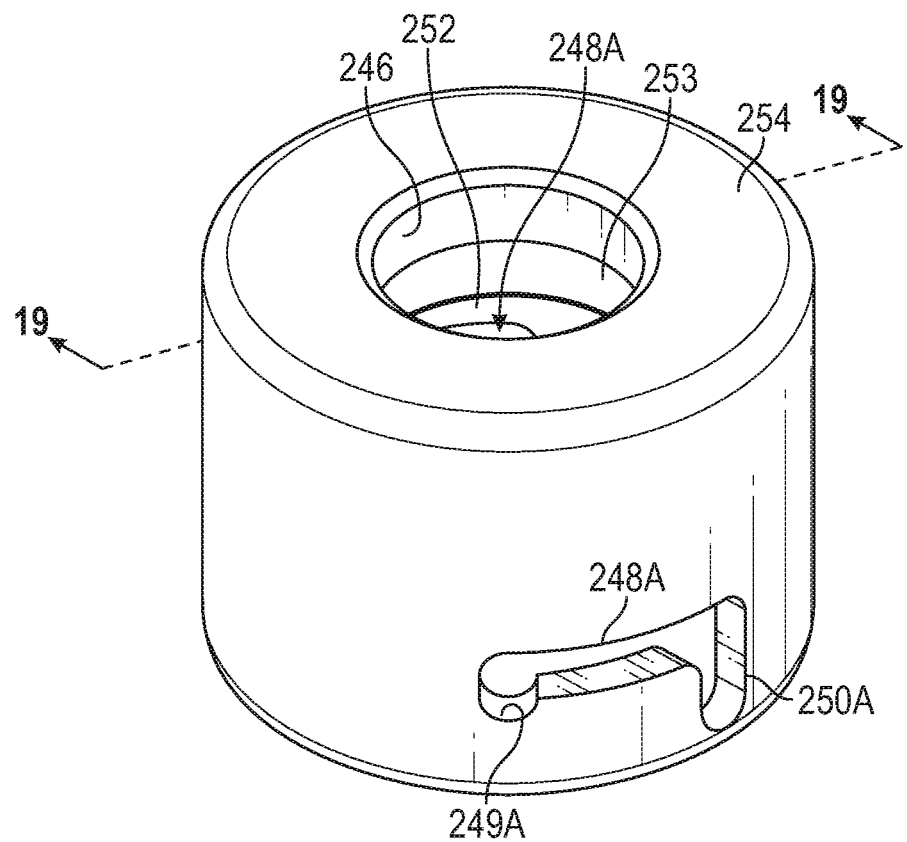
FIG. 18 is a perspective view of the locking collar of FIGS. 13-15B showing a pin slot.
Figure 19:
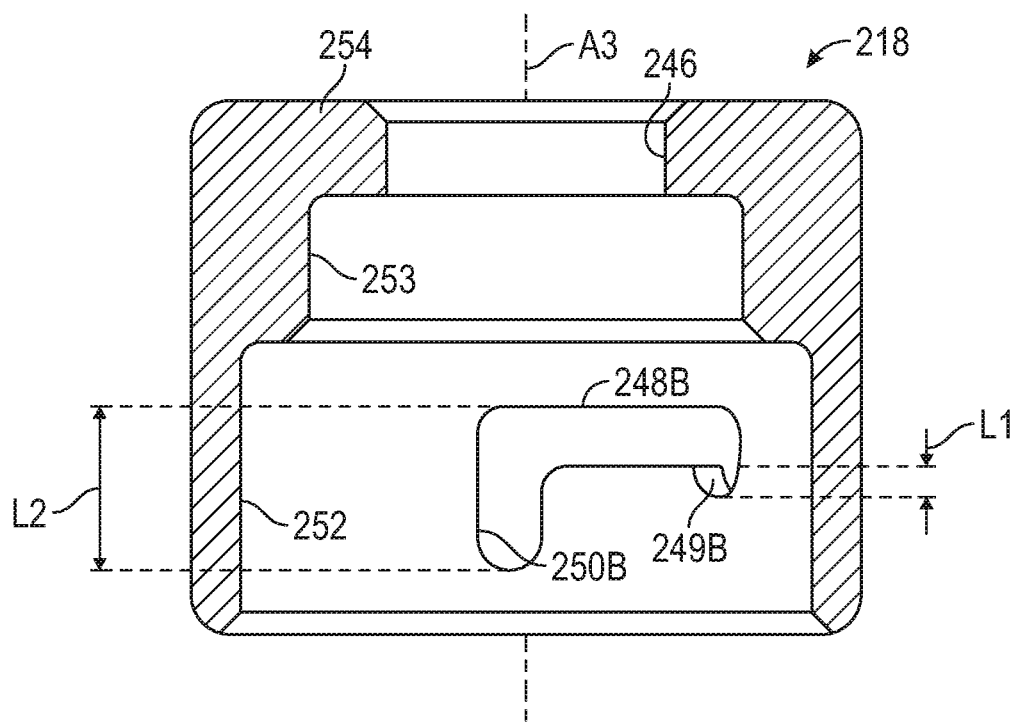
FIG. 19 is a cross-sectional view of the locking collar of FIG. 18 showing concentric lands within an inner cavity of the locking collar.

FIG. 15A is a cross-sectional view of derotator 210 of FIG. 13 showing locking collar 218 in a position to prevent movement of handle 212 relative to shaft 214. Handle coupler 219 is shown pushed against shaft coupler 220 by force of spring 224. Spring 224 is positioned between locking collar 218 and pivot portion 240 of handle coupler 219. Locking collar 218 can include shaft bore 246, slide pocket 252, spring pocket 253 and end wall 254. (Note that spring 224 is shown in an expanded position extending through locking collar 218 for illustrative purposes in FIGS. 13, 15A and 15B. In actuality, spring 224 would be compressed between pivot portion 240 and end wall 254 inside of locking collar 218.) Spring 224 can push against end wall 254 to force pivot portion 240 toward shaft 214 (to the left in FIG. 15A). Fingers 226 engage shelf 228 to lock the angular position of handle coupler 219 relative to pin 222. Pin 222 is forced to the rear (right-most portion with reference to FIG. 15A) of slot 244 via engagement with short ends 249A and 249B of slots 248A and 248B (FIGS. 18 and 19). As such, the rear of slot 244 and short ends 249A and 249B are aligned such that pivot portion 240 abuts spring pocket 253. In other words, short ends 249A and 249B (FIGS. 18 and 19) are aligned with bores 234A and 234B (FIG. 14) in shaft coupler 220 thereby locking the translational position of locking collar 218 and shaft coupler 220 with handle coupler 219 wedged between shelf 228 and the face of spring pocket 253. Thus, handle coupler 219 cannot slide on pin 222 at slot 244, e.g., pivot portion 240 cannot slide within slide pocket 252.

However, when locking collar 218 is rotated, such as via an operator action, so that long ends 250A and 250B are aligned with bores 234A and 234B in shaft coupler 220, handle coupler 219 can slide on pin 222 at slot 244. Thus, handle coupler 219 can be pulled away from shaft coupler 220 and fingers 226 can be disengaged from shelf 228, as is discussed with reference to FIG. 15B.

FIG. 15B is a cross-sectional view of derotator 210 of FIG. 13 showing locking collar 218 in a position to allow movement of handle 212 relative to shaft 214. Locking collar 218 is rotated to align long ends 250A and 250B (FIGS. 18 and 19) with pin 222. As such, spring 224 can expand to push locking collar 218 rearward (to the right with reference to FIG. 15B) along long ends 250A and 250B. Thus, the face of spring pocket 253 can move away from pivot portion 240 and handle coupler 219 can become unlocked and uncompressed against pin 222. Thus, an operator of derotator 210 can pull handle 212 rearward (to the right with reference to FIG. 15B) to slide handle coupler 219 along pin 222 at slot 244 so that pivot portion 240 again engages the face of spring pocket 253 and spring 224 becomes compressed. With handle coupler 219 translated rearward, fingers 226 can disengage from shelf 228 and handle coupler 219 can pivot on pin 222 at the forward most end of slot 244. Handle 212 can thus be rotated along arc Ac (FIG. 13) to reposition a different pair of fingers 226 adjacent shelf 228. Handle 212 can be released to reengage shelf 228 with fingers 226 to lock handle 212 into an arcuate position relative to shaft 214, thereby again moving pivot portion 240 away from the face of spring pocket 253 as illustrated in FIG. 15B. Locking collar 218 can then be moved back to the locked position of FIG. 15A by pushing locking collar 218 forward (to the left with reference to FIG. 15B) to compress spring 224 and reengage the face of spring pocket 253, and rotating locking collar 218 to slide pin 222 along 248A and 248B from long ends 250A and 250B to short ends 249A and 249B.

Figure 16:
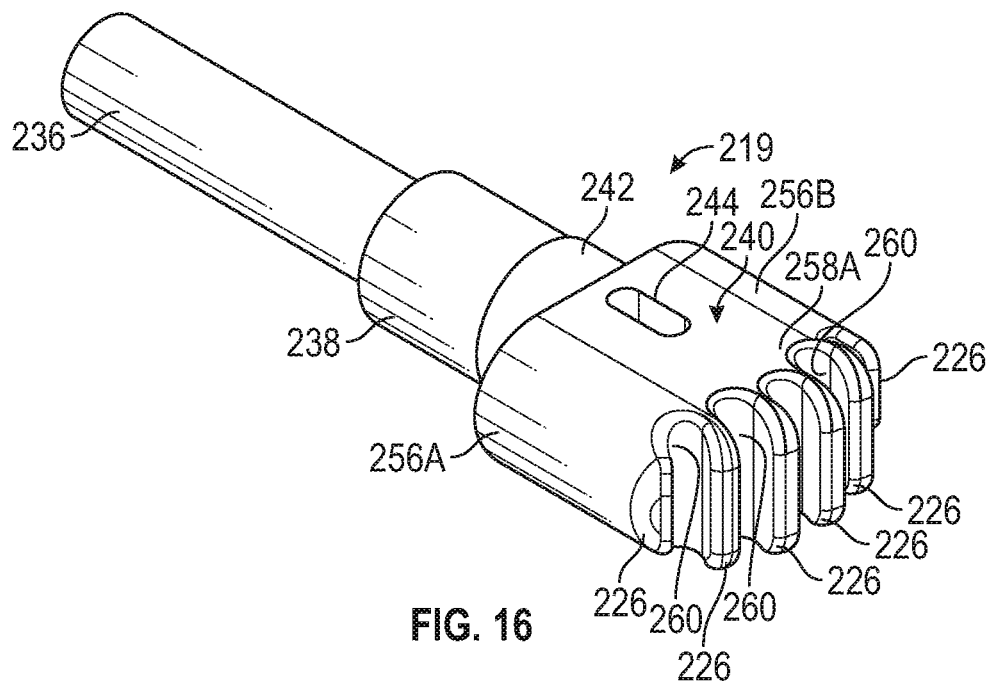
FIG. 16 is a perspective view of a handle coupler of the derotator FIG. 13-15B showing fingers for positioning the handle in five different locations.

FIG. 16 is a perspective view of handle coupler 219 of FIG. 13-15B showing fingers 226 for positioning handle 212 in five different locations. As mentioned, handle coupler 219 can include shaft portion 236, slide portion 238, pivot portion 240, land 242 and slot 244.

Shaft portion 236 can comprise an elongate portion that is configured to engage coupling bore 251 (FIG. 15A) in handle 212. Shaft portion 236 and coupling bore 251 can have the same shaped cross-sectional profiles. In the illustrated embodiment, shaft portion 236 is cylindrical and has a circular cross-sectional profile. As discussed below with reference to FIG. 22, shaft portion 236 and coupling bore 251 can have other shapes, such as square, to inhibit rotation between handle 212 and handle coupler 219. An interference or force fit between shaft portion 236 and coupling bore 251 can be provided. Additionally, shaft portion 236 and coupling bore 251 can be connected via a threaded engagement in other embodiments.

Slide portion 238 can comprise a cylindrical extension of shaft portion 236 with a larger diameter. Slide portion 238 can be configured to slide within shaft bore 246 of locking collar 218. As such, slide portion 238 and shaft bore 246 can have circular cross-sectional profiles to facilitate sliding and rotation of locking collar 218 about slide portion 238. Slide portion 238 can have a diameter that is slightly smaller than the diameter of shaft bore 246.

Land 242 can comprise a location for receiving spring 224. Land 242 can comprise a short segment of slide portion 238 configured having a slightly larger diameter than slide portion 238, but can be small enough to receive the inner diameter of the coils of spring 224. Coils of spring 224 can be expanded to fit around land 242. The length of land 242 can be sufficient to receive one or more coils of spring 224. Thus, the coils of spring 224 wrapped around land 242 can hold spring 224 in place to, among other things, facilitate assembly of derotator 212.

Pivot portion 240 can be configured to slide within slide pocket 252 of locking collar 218. As such, pivot portion 240 and slide pocket 252 can have circular cross-sectional profiles to facilitate sliding and rotation of locking collar 218 about pivot portion 240. Pivot portion 240 can have arcuate panels 256A and 256B at opposite ends that form part of the circular cross-sectional profile and to facilitate slide and rotating within collar 218. Arcuate panels 256A and 256B of pivot portion 240 can have a diameter that is slightly smaller than the diameter of slide pocket 252. However, pivot portion 240 can have flattened side panels 258A and 258B (not visible in FIG. 16) to permit prongs 232A and 232B of shaft coupler 220 to be received within locking collar 218 at the same time as pivot portion 240, as shown in FIG. 13.

Fingers 226 can extend from an end of pivot portion 240. Troughs 260 can be formed between adjacent fingers 226 on pivot portion 240. The distance between fingers can correspond to the thickness of shelf 228 to facilitate handle coupler 219 tightly engaging with shaft coupler 220. Troughs 260 can be distributed along an arc length that is concentric with pin 222 to facilitate rotation of handle coupler 219 along arc Ac of FIG. 13. Likewise the distal tips of fingers 226 can be distributed along an arc length concentric with pin 222 and arc Ac of FIG. 13 to facilitate fingers 226 being able to move past shelf 228 when handle 212 is being rotated. In the illustrated embodiment, handle coupler 219 includes six fingers 226 that form five troughs 260 to position handle 212 along a forty-five degree arc length in five positions that are fifteen degrees apart. However, in other embodiments, handle coupler 218 can have more or fewer fingers to position handle 212 along a greater or smaller arc length. The thickness of shelf 228 and fingers 226 can be varied to provide greater or smaller arc length increments. That is, a thinner shelf 228 and smaller troughs 260 can provide smaller locking segments than fifteen degrees and a thicker shelf 228 and larger troughs 260 can provide larger locking segments than fifteen degrees. The thickness of shelf 228 and fingers 226 for controlling movement of handle 212 can be balanced with providing sufficient structural stability to articulating coupling 216.

Figure 17:
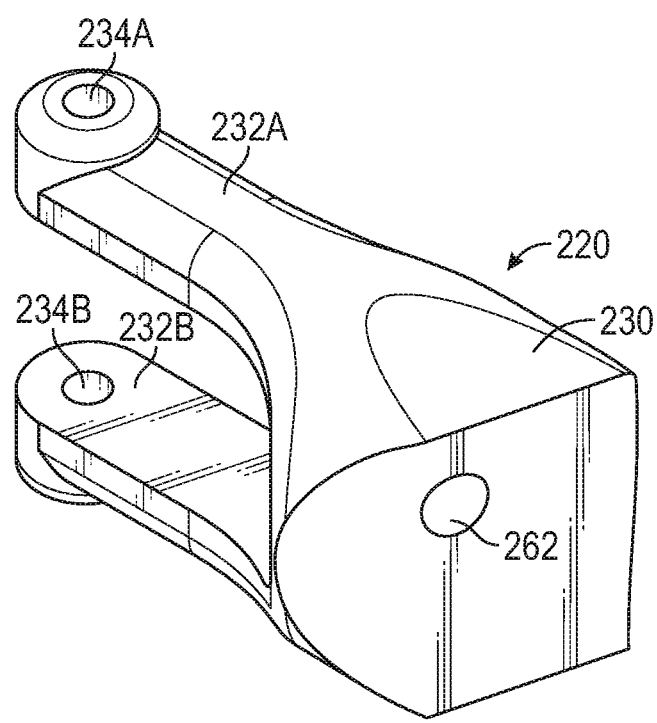
FIG. 17 is a perspective view of a shaft coupler of the derotator of FIG. 13 for pivotably coupling the shaft to the handle coupler.

FIG. 17 is a perspective view of shaft coupler 220 of derotator 210 of FIG. 13 for pivotably coupling handle 212 to shaft 214. Shaft coupler 220 can include base 230 for attaching to shaft 214 and prongs 232A and 232B that extend from base 230 to receive pin 222. Shelf 228 (not visible in FIG. 17, see FIG. 14) can extend from base 230 between prongs 232A and 232B. Prongs 232A and 232B can include bores 234A and 234B, respectively, that can receive pin 222. Prongs 232A and 232B can be reinforced at bores 234A and 234B. Base 230 can be attached to shaft 214 via any suitable method or means. For example, base 230 can be welded or brazed to shaft 214, or bonded with adhesive. Base 230 can include bore 262 that can be configured to align with bore 264 (FIG. 15B) in shaft 214. Bores 262 and 264 can be configured to receive pin 266 (FIG. 15B) to facilitate coupling of base 230 to shaft 214. Base 230 can also be formed integrally with shaft 214 is other embodiments.

Base 240 can be shaped to position handle coupler 219 at an angle to shaft 214 when handle coupler 219 is centered on shelf 228, as can be seen in FIGS. 15A and 15B. That is, shaft portion 236 can extend along an axis, that when aligned with an axis extending along the center of shelf 228, can be at an angle to the center axis of shaft 214. In an example, the axis of shelf 228 and shaft 214 can be configured the same as central axes A1 and A2 discussed above with reference to FIGS. 1 and 7. Shaft 214 can be configured the same as various embodiments of shaft 14 discussed above.

FIG. 18 is a perspective view of locking collar 218 of FIGS. 13-15B showing pin slot 248A. FIG. 19 is a cross-sectional view of locking collar 218 of FIG. 18 showing concentric lands forming shaft bore 246, spring pocket 253 and slide pocket 252 within an inner cavity of locking collar 218. FIGS. 18 and 19 are discussed concurrently.

Locking collar 218 can include shaft bore 246, slide pocket 252, spring pocket 253 and end wall 254. Slots 248A and 248B can include short ends 249A and 249B and long ends 250A and 250B. As discussed above, shaft bore 246 can be configured to interact with shaft portion 236 of handle coupler 219, spring pocket 253 can be configured to receive spring 224, and slide pocket 252 can be configured to interact with pivot portion 240 of handle coupler 219.

Slots 248A and 248B can comprise arcuate slots extending along the portion of locking collar 218 that forms slide pocket 252. The arcuate slots can extend concentrically with the walls of slide pocket 252 to permit locking collar 218 to rotate about pivot portion 240. Short ends 249A and 249B and long ends 250A and 250B can comprise elongations of slots 248A and 248B transverse to slots 248A and 248B, respectively. In other words, short ends 249A and 249B and long ends 250A and 250B can extend axially in the direction of central axis A3 of locking collar 218. The length of short ends 249A and 249B can be sufficient to inhibit locking collar 218 from rotating circumferentially. That is, short ends 249A and 249B can be equivalent to only the width of slots 248A and 248B, respectively, to provide the locking described above with reference to FIG. 15A. However, short ends 249A and 249B can comprise a slight widening of slots 248A and 248B to provide a locking effect that inhibits locking collar 218 from undesirably (e.g., unintentionally) rotating to the unlocked position of FIG. 15B. Thus, in an embodiment, short ends 249A and 249B can extend out from slots 248A and 248B, respectively, a length L1 equal to approximately half the width of pin 222. Long ends 250A and 250B can extend out from slots 248A and 248B, respectively, a length sufficient to allow handle coupler 219 to be withdrawn from shelf 228. Thus, in an embodiment, the total length L2 of long ends 250A and 250B, including the width of slots 248A and 248B, can be equal to the length of slot 244 in pivot portion 240.

Figure 20:
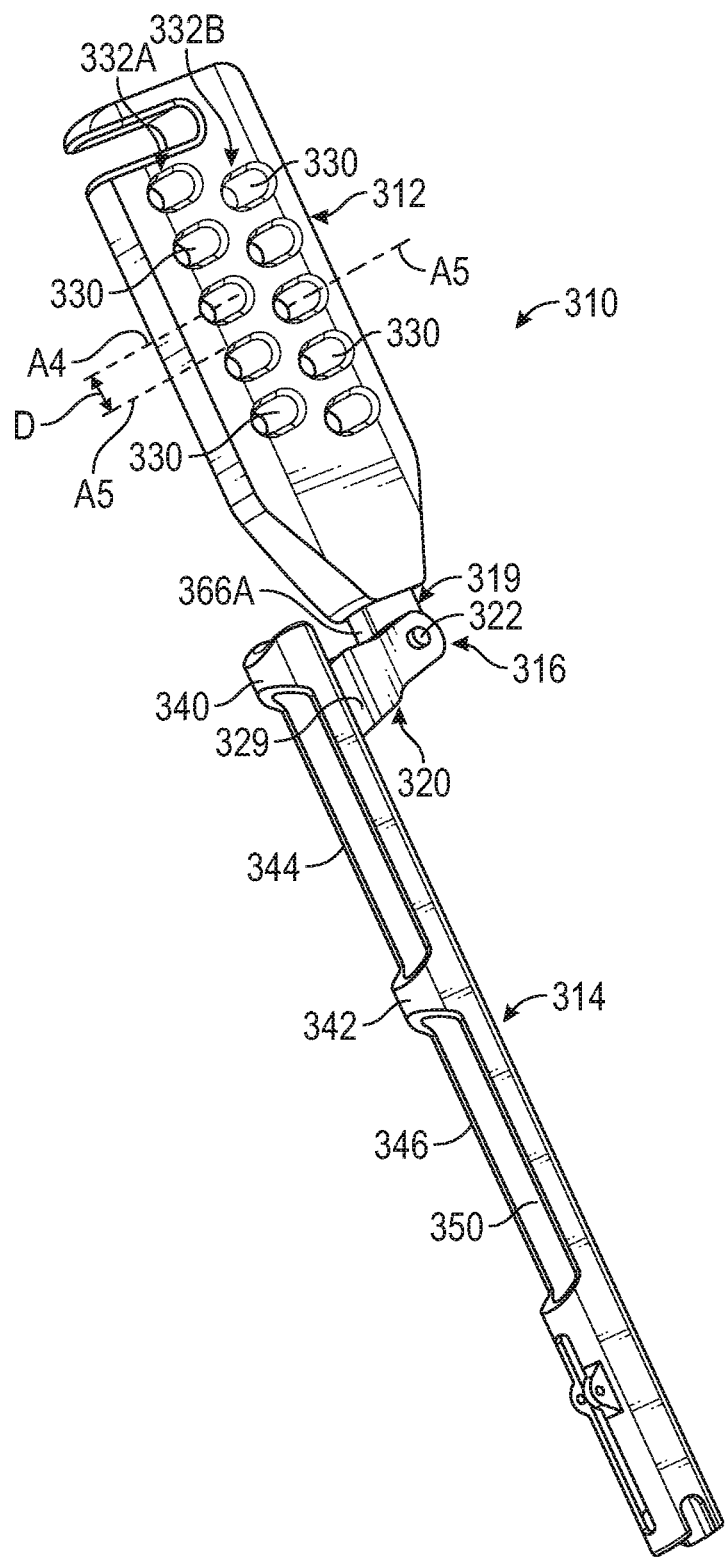
FIG. 20 is a front perspective view of a derotator according to the present disclosure having a handle and shaft connected by an articulating coupling having a freely moving hinge coupling.
Figure 21:
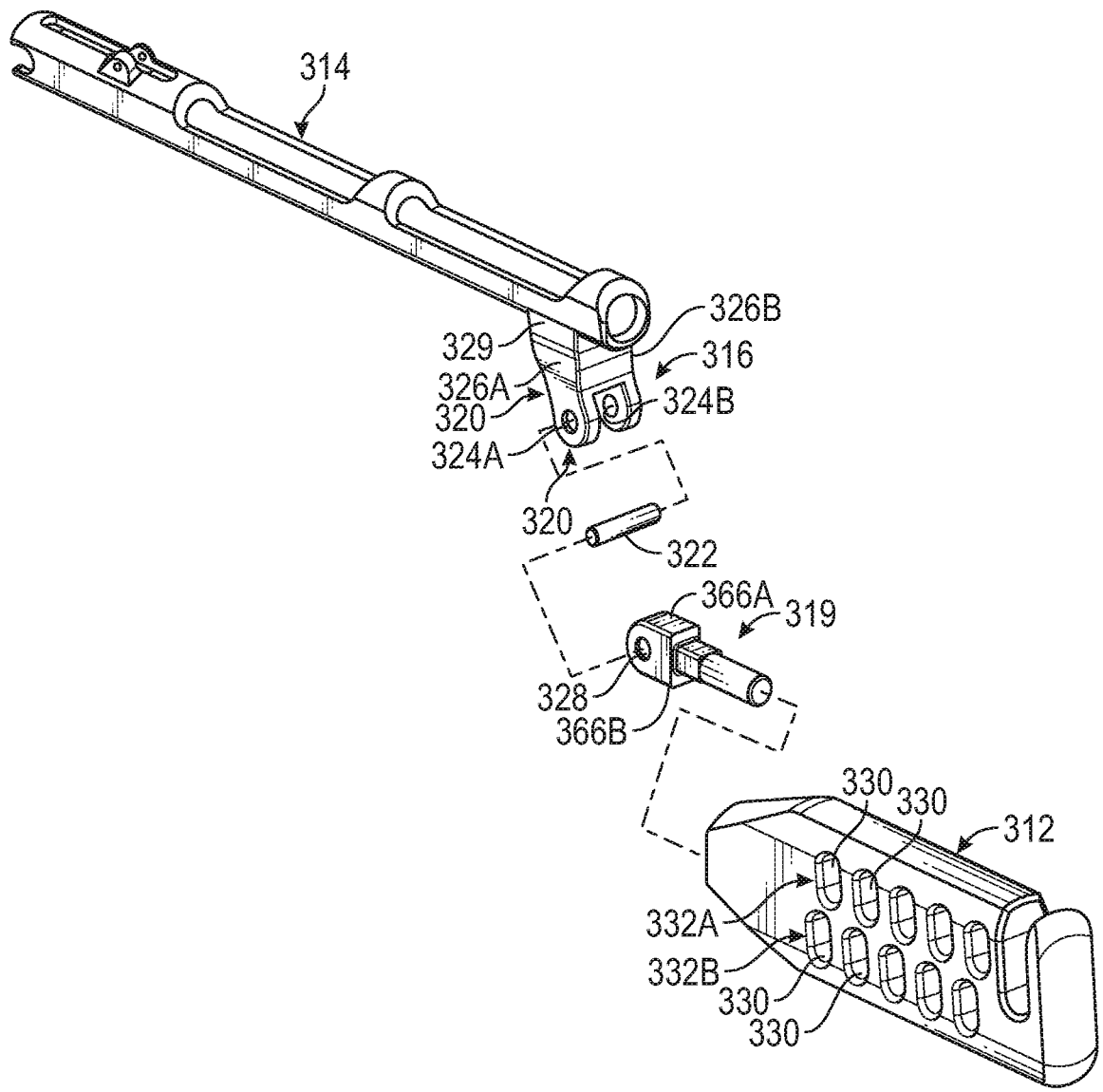
FIG. 21 is an exploded view of the derotator of FIG. 20 showing components of the freely moving hinge coupling.

FIG. 20 is a front perspective view of a derotator 310 according to the present disclosure having handle 312 and shaft 314 connected by articulating coupling 316 having a freely moving hinge coupling between handle coupler 319 and shaft coupler 320 at pin 322. FIG. 21 is an exploded view of derotator 310 of FIG. 20 showing components of the freely moving hinge coupling. FIGS. 20 and 21 are discussed concurrently.

Shaft coupler 320 can comprise a yoke for receiving handle coupler 319. Pin 322 can be inserted through bores 324A and 324B in prongs 326A and 326B of shaft coupler 320 and bore 328 of handle coupler 319 to facilitate rotation of shaft 314 and handle 312 relative to each other. Prongs 326A and 326B can extend from base 329 of shaft coupler 320. Base 329 can be attached to shaft 314 via any suitable means or methods. The diameters of bores 324A, 324B and 328 can be the same such that handle coupler 319 does not translate relative to shaft coupler 320. Pin 322 can allow handle 312 to rotate into any position along an arcuate path between extreme end positions that can be controlled by engagement of handle coupler 319 with shaft coupler 320 in a rotated out position (as shown in FIG. 20) and engagement of handle 312 with shaft 314 in a rotated in position, as is discussed in greater detail with reference to FIG. 23.

Handle 312 can include offset slots 330 that can be arranged in rows 332A and 332B. Slots 330 in row 332A can be offset from slots 330 in row 332B. That is the centers of slots 330 in row 332A along axis A4 can be shifted a distance D away from the centers of slots 330 in row 332B along axis A5. As such, handle 312 is rotated in use, such as can be done in accord with the procedure discussed with reference to FIGS. 11A-11D, various slots 330 can align with linkage rods 134 and alignment rods 138 to accommodate spinal rods 132 that are not aligned. By providing slots 330 that are shorter than slots 58A-58E (FIG. 1), handles 312 can be locked to other derotators of derotator series, e.g., series derotator series LT and RT of FIG. 11C, to perform spinal procedures. Shorter slots 330 can provide an additional degree of locking compared to longer slots 330. Shorter slots 330 can be more difficult to align with rods 134 and 138, but a greater number of shorter slots 330 can be provided on handle 312 to provide a greater number of locking locations. For example, handle 312 can be provided with three row of circular slots 330, with the centers of the circles in each row offset from the centers of the circles in the other rows. Thus, derotator 310 need not be individually locked, e.g. the position of handle 312 relative to shaft 314 need not be locked, in order for derotator 310 to be used with other fixed or locked derotators. As an example, derotator 310, or any of the derotators described herein, can be used with a group of fixed derotators, and derotator 310 can be used to couple to particularly misaligned portions of a spine. Derotator 310 can assist in providing derotation force even though handle 312 is not locked in position relative to shaft 314 because, among other things, slots 330 have a width that is approximately the same size as rods 134 and 138 and slots 58, thus allowing rotational force about spine S (FIG. 11C) to still be applied.

Shaft 314 can include loops 340 and 342 and cut-outs 344 and 346 disposed along channel 350. Channel 350 can function similarly to channel 50 of shaft 14 of FIG. 4. Channel 350 can allow a fastener, including a fastener having a head or a housing, to pass through shaft 14, and allow a driver instrument, such as a screw driver, to be inserted through shaft 14 to reach drive features, such as a hex head, hexalobe head, torx head or pentalobe head, of a fastener connected to the bone anchor housing. Loops 340 and 342 can facilitate insertion and alignment of the driver instrument and fastener into channel 350, thereby preventing or limiting misalignment of the fastener when being inserted into bone. Loops 340 and 342 can be advantageous over fully covering or enclosing channel 350 due to cleanability. That is, loops 340 and 342 facilitate alignment of surgical hardware and instrumentation, but permit access to the length of channel 350 to allow shaft 314 to be cleaned and sterilized for reuse.

Figure 22:
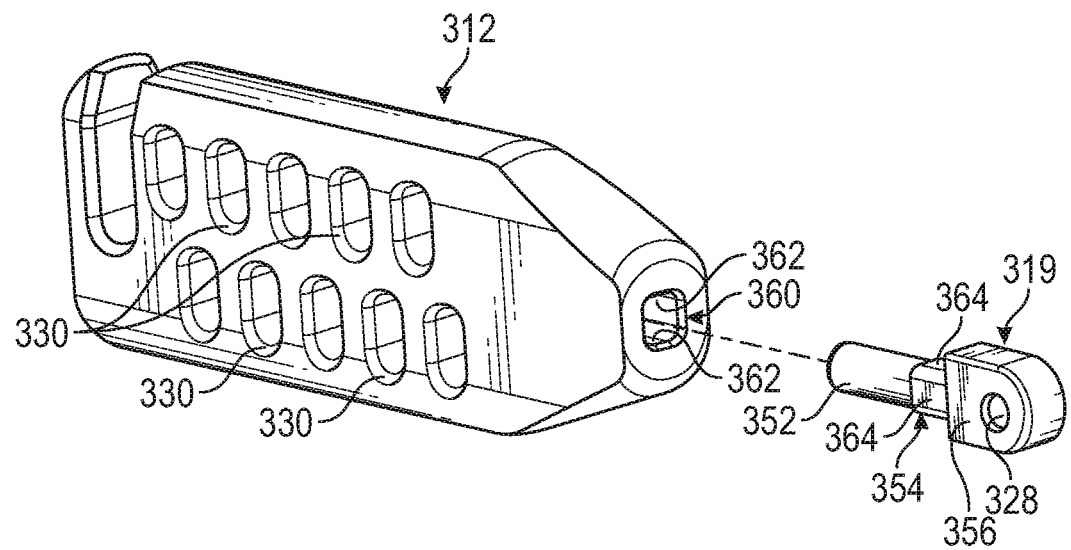
FIG. 22 is an exploded view of a handle coupler of the freely moving hinge coupling of FIG. 21 and the handle of FIG. 20.

FIG. 22 is an exploded view of handle coupler 319 of the freely moving hinge coupling of FIG. 21 and handle 312 of FIG. 20. Handle coupler 319 can include shaft portion 352, neck portion 354, rotation portion 356 and bore 328. Handle 312 can include socket 360, which can include planar walls 362 and a cylindrical socket (not visible in FIG. 22) extending further into handle 312 past planar walls 362. Shaft portion 352 of handle coupler 319 can extend into the cylindrical socket of socket 360 and neck portion 354 of handle coupler 319 can extend into the cavity defined by planar walls 362. Engagement of planar walls 362 of socket 360 with mating planar walls 364 of neck portion 354 on handle coupler 319 can prevent relative rotation of handle 312 relative to handle coupler 319, thereby facilitating the major surfaces of handle 312 being aligned parallel to the axis of shaft 314. This can facilitate axes extending through slots 330 being aligned perpendicular to the axis of shaft 314. Planar walls 364 can be chamfered to facilitate entry of neck portion 354 into socket 360.

Figure 23:
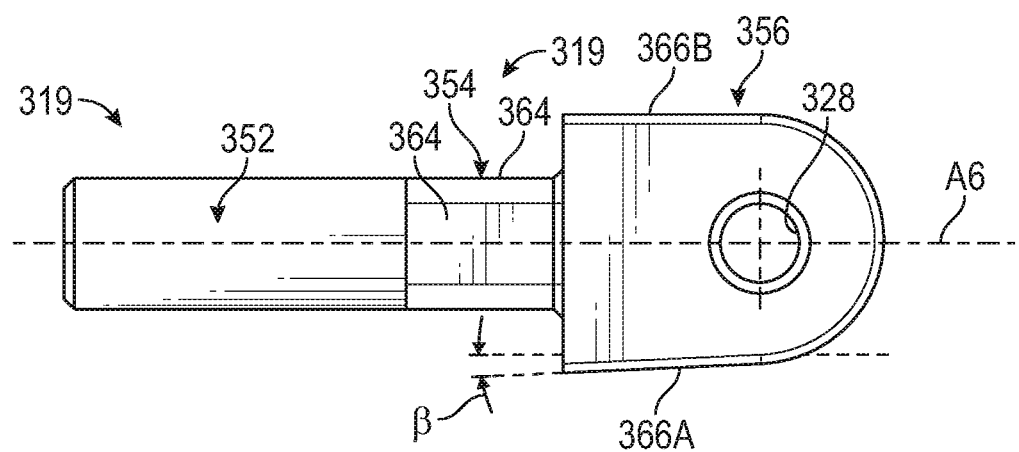
FIG. 23 is a side view of the handle coupler of FIGS. 20-22 showing tapered side surfaces for limiting movement of the freely moving hinge coupling.

FIG. 23 is a side view of handle coupler 319 of FIGS. 20-22 showing tapered side surfaces 366A and 366B for limiting movement of the freely moving hinge coupling. One of both of side surfaces 366A and 366B can be configured to engage base 329 of shaft coupler 320 (FIGS. 20 and 21). Side surface 366A can be configured to face toward the end of shaft 314 closest to shaft coupler 320 when handle coupler 319 is connected to shaft coupler 320. Side surface 366B can be configured to face toward the end of shaft 314 furthest away from shaft coupler 320 when handle coupler 319 is connected to shaft coupler 320. Side surface 366B can be parallel to central axis A6 of handle coupler 319. As such, side surface 366B will not contact base 329 of shaft coupler 320 and handle 312 will be free to rotate down toward shaft 314 until handle 312 engages shaft 314. Side surface 366A can be disposed at angle R relative to central axis A6 of handle coupler 319. As such, side surface 366A can contact base 329 of shaft coupler 320 before handle 312 contacts the end of shaft 314 closest to base 329. As shown in FIG. 20, side surface 366A can be configured to stop movement of handle 312 when the central axis of handle 312 is approximately perpendicular to the central axis of shaft 314. In an example, angle 3 can be approximately three degrees.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure. For example, the details of shaft 14 can be incorporated into shafts 214 and 314 and vice versa. Additionally, any of derotators 10, 210 and 310 can be used in the method discussed with reference to FIG. 12. Likewise, the locking collar 218 and variations thereof can be used in combination with derotators 10 and 310.

VARIOUS NOTES & EXAMPLES

Example 1 can include or use subject matter such as a surgical derotator instrument comprising: a shaft, a handle and an articulating coupler. The shaft can comprise: a first end portion having a bone anchor coupling; and a second end portion opposite the first end portion. The handle can comprise: a body portion; and a slot extending in the body portion; and an articulating coupler connecting the shaft and the handle.

Example 2 can include, or can optionally be combined with the subject matter of Example 1, to optionally include a shaft and a handle that can be disposed in a plane and the articulating coupler provides for rotation of the handle relative to the shaft in the plane.

Example 3 can include, or can optionally be combined with the subject matter of one or any combination of Examples 1 and 2 to optionally include a handle that can include a plurality of slots disposed in the plane.

Example 4 can include, or can optionally be combined with the subject matter of one or any combination of Examples 1 through 3 to optionally include a plurality of slots includes a first row of slots and a second row of slots, wherein centers of slots in the first row are offset from centers of slots in the second row.

Example 5 can include, or can optionally be combined with the subject matter of one or any combination of Examples 1 through 4 to optionally include a shaft that can further comprise a neck extending from the second end portion at an oblique angle in the plane, the neck configured to receive the articulating coupler.

Example 6 can include, or can optionally be combined with the subject matter of one or any combination of Examples 1 through 5 to optionally include an articulating coupler that can permit the handle to be rotated freely between a first end position and a second end position.

Example 7 can include, or can optionally be combined with the subject matter of one or any combination of Examples 1 through 5 to optionally include a handle that can be rotated into a plurality of discrete positions in the plane.

Example 8 can include, or can optionally be combined with the subject matter of one or any combination of Examples 1 through 5 and 7 to optionally include an articulating coupler that can be spring biased to lock the articulating coupler into each of the plurality of discrete positions.

Example 9 can include, or can optionally be combined with the subject matter of one or any combination of Examples 1 through 8 to optionally include an articulating coupler that can comprise: a handle coupler connected to the body of the handle; a shaft coupler connected to the shaft; and a first pin coupling the handle coupler to the shaft coupler.

Example 10 can include, or can optionally be combined with the subject matter of one or any combination of Examples 1 through 5 and 7 through 9 to optionally include a shaft coupler that can include a shelf, and a handle coupler that can include a plurality of fingers forming a plurality of troughs configured to receive the shelf.

Example 11 can include, or can optionally be combined with the subject matter of one or any combination of Examples 1 through 5 and 7 through 9 to optionally include an articulating coupler that can further comprise: an angled lock disposed between the handle coupler and the shaft coupler; and a spring positioned around a portion of the angled lock; wherein the first pin extends through the angled lock.

Example 12 can include, or can optionally be combined with the subject matter of one or any combination of Examples 1 through 5, 7, 8, 9 and 11 to optionally include an angled lock that can comprise: a stem having: a first end; a second end; and a first aperture disposed between the first and second ends; and first and second projections extending from one of the first and second ends of the stem; wherein the spring is disposed around the stem, and the first pin extends through the first aperture.

Example 13 can include, or can optionally be combined with the subject matter of one or any combination of Examples 1 through 5, 7, 8, 9, 11 and 12 to optionally include a second pin; a first pin hole in the handle coupler; a second pin hole in the handle coupler; and a second aperture in the shaft coupler; wherein the first pin extends through the first pin hole, the first aperture and the second aperture; and wherein the second pin extends through the second pin hole between the first and second projections of the angled lock.

Example 14 can include, or can optionally be combined with the subject matter of one or any combination of Examples 1 through 5, 7, 8, 9, 11, 12 and 13 to optionally include: a third pin; a third pin hole in the shaft coupler; and a fourth pin hole located between the first and second ends of the stem; wherein the third pin extends through the third pin hole and the fourth pin hole.

Example 15 can include, or can optionally be combined with the subject matter of one or any combination of Examples 1 through 5, 7, 8, 9, 11, 12, 13 and 14 to optionally include first and second projections that can comprise teeth.

Example 16 can include, or can optionally be combined with the subject matter of one or any combination of Examples 1 through 5, 7, 8, 9, 11, 12, 13, 14 and 15 to optionally include the second end portion of the shaft that can include a first socket for receiving the shaft coupler; and the body portion of the handle that can include a second socket for receiving the handle coupler.

Example 17 can include, or can optionally be combined with the subject matter of one or any combination of Examples 1 through 16 to optionally include a locking mechanism configured to prevent the handle coupler from rotating relative to the shaft coupler in the plane.

Example 18 can include, or can optionally be combined with the subject matter of one or any combination of Examples 1 through 17 to optionally include a locking mechanism configured to prevent the handle coupler from translating relative to the shaft coupler.

Example 19 can include, or can optionally be combined with the subject matter of one or any combination of Examples 1 through 18 to optionally include a locking mechanism that can comprise a collar attached to the pin configured to inhibit translation of either the handle coupler or the shaft coupler on the pin.

Example 20 can include, or can optionally be combined with the subject matter of one or any combination of Examples 1 through 19 to optionally include a bone anchor coupling that can comprise: a socket configured to receive a housing of a bone anchor, and a spring-loaded detent mechanism attached to the shaft adjacent the socket to releasably secure the housing of the bone anchor when the bone anchor is attached to the socket.

Example 21 can include, or can optionally be combined with the subject matter of one or any combination of Examples 1 through 20 to optionally include a shaft that can be hollow and configured to deliver a fastener to the bone anchor coupling.

Example 22 can include, or can optionally be combined with the subject matter of one or any combination of Examples 1 through 21 to optionally include a shaft that can include cut-outs to allow access to an interior of the shaft, and loops disposed adjacent the cut-outs to facilitate delivery of the fastener.

Example 23 can include or use subject matter such as a surgical instrument comprising: a lever having a first end and a second end; a bone anchor attachment mechanism connected to the lever proximate the first end; an articulating coupler connected to the lever proximate the second end; and a slotted handle connected to the articulating coupler.

Example 24 can include, or can optionally be combined with the subject matter of Example 23, to optionally include an articulating coupler that permits the handle to rotate relative to the shaft in only one plane.

Example 25 can include, or can optionally be combined with the subject matter of one or any combination of Examples 23 and 24 to optionally include an articulating coupler that can include a spring loaded detent mechanism to lock the handle into one of a plurality of discrete angular positions relative to the shaft.

Example 26 can include, or can optionally be combined with the subject matter of one or any combination of Examples 23 through 25 to optionally include a locking mechanism configured to selectively prevent a spring loaded detent mechanism from disengaging.

Example 27 can include or use subject matter such as a method for coupling a plurality of derotator instruments into a series of a plurality of derotator instruments, the method comprising: attaching a plurality of derotator instruments to a plurality of adjacent bone anchors, each derotator instrument comprising: a shaft for connecting to a bone anchor; a handle having a slot; and an adjustable coupler connecting the shaft and the handle; adjusting one or more of the adjustable couplers to align at least one of the slots of the series with other slots of the series; and inserting an elongate member through the at least one slots that are aligned.

Example 28 can include, or can optionally be combined with the subject matter of Example 27, to optionally include adjusting one or more of the adjustable couplers can comprise: moving a first handle into one of a plurality of discrete positions relative to a first shaft via a first adjustable coupler connecting the first shaft and the first handle.

Example 29 can include, or can optionally be combined with the subject matter of one or any combination of Examples 27 and 28 to optionally include adjusting one or more of the adjustable couplers can further comprise: pulling the first handle away from the first shaft to overcome a spring force in the first adjustable coupler, pivoting the first handle to align a first catch with one of a plurality of slots within the first adjustable coupler; and releasing the first handle and inserting the first catch into the one of the plurality of slots within the first adjustable coupler.

Example 30 can include, or can optionally be combined with the subject matter of one or any combination of Examples 27 through 29 to optionally include unlocking the first handle to permit the spring force to be overcome.

Example 31 can include, or can optionally be combined with the subject matter of one or any combination of Examples 27 through 30 to optionally include unlocking the first handle comprises rotating a locking collar to an unconstrained position.

Example 32 can include, or can optionally be combined with the subject matter of one or any combination of Examples 27 through 31 to optionally include a plurality of discrete positions that can be located in a plane containing the first handle and the first shaft.

Example 33 can include, or can optionally be combined with the subject matter of one or any combination of Examples 27 through 32 to optionally include inserting an elongate member that can comprise inserting a pin through the at least one slots that are aligned.

Example 34 can include, or can optionally be combined with the subject matter of one or any combination of Examples 27 through 33 to optionally include inserting the plurality of adjacent bone anchors through the shafts of the plurality of adjacent derotator instruments before attaching the plurality of derotator instruments to the plurality of adjacent bone anchors.

Example 35 can include, or can optionally be combined with the subject matter of one or any combination of Examples 27 through 34 to optionally include a attaching multiple sets of derotator instruments to multiple sets of bone anchors.

Example 36 can include, or can optionally be combined with the subject matter of one or any combination of Examples 27 through 35 to optionally include manipulating the multiple sets of derotator instruments to align heads of the multiple sets of bone anchors.

Example 37 can include, or can optionally be combined with the subject matter of one or any combination of Examples 27 through 36 to optionally include placing a rod through the heads of the multiple sets of bone anchors.

Example 38 can include, or can optionally be combined with the subject matter of one or any combination of Examples 27 through 37 to optionally include passing a set screw to each bone anchor through hollow shafts of each derotator instrument.

Each of these non-limiting examples can stand on its own, or can be combined in various permutations or combinations with one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. A method for coupling a plurality of derotator instruments into a series of a plurality of derotator instruments, the method comprising:
attaching a plurality of derotator instruments to a plurality of adjacent bone anchors, each derotator instrument comprising:
a shaft for connecting to a bone anchor;
a handle having a slot; and
an adjustable coupler pivotally connecting the shaft and the handle thereby enabling motion of the slot relative to the shaft;
adjusting one or more of the adjustable couplers to align at least one of the slots of the plurality of derotator instruments with at least one other slot of the plurality of derotator instruments, wherein adjusting comprises:
moving a first handle into one of a plurality of discrete positions relative to a first shaft via a first adjustable coupler connecting the first shaft and the first handle;
pulling a first handle away from a first shaft to overcome a spring force in a first adjustable coupler connecting the first shaft and the first handle;
pivoting the first handle to align a first catch with one of a plurality of slots within the first adjustable coupler; and
releasing the first handle and inserting the first catch into the one of the plurality of slots within the first adjustable coupler; and
inserting an elongate member through two or more slots of the plurality of derotator instruments that are aligned.

2. The method of claim 1, wherein adjusting one or more of the adjustable couplers comprises:
moving the first handle into one of a plurality of discrete positions relative to the first shaft via the first adjustable coupler.

3. The method of claim 2, wherein the plurality of discrete positions are located in a plane containing the first handle and the first shaft.

4. The method of claim 1, further comprising unlocking the first handle to permit the spring force to be overcome.

5. The method of claim 4, wherein unlocking the first handle comprises rotating a locking collar to an unconstrained position.

6. The method of claim 1, wherein the inserting comprises inserting a pin through the two or more slots of the plurality of derotator instruments that are aligned.

7. The method of claim 1, further comprising inserting the plurality of adjacent bone anchors through the shafts of the plurality of adjacent derotator instruments before inserting the elongate member through the two or more slots of the plurality of derotator instruments that are aligned.

8. The method of claim 7, further comprising linking two or more of the plurality of derotator instruments, wherein the two or more of the plurality of derotator instruments each comprise a slot in the two or more slots of the plurality of derotator instruments that are aligned.

9. The method of claim 8, further comprising aligning heads of multiple sets of bone anchors.

10. The method of claim 9, further comprising placing a rod through the heads of the multiple sets of bone anchors.

11. The method of claim 10, further comprising passing a set screw to each bone anchor through hollow shafts of each derotator instrument.

12. A method for coupling a plurality of derotator instruments into a series of a plurality of derotator instruments, the method comprising:
attaching a plurality of derotator instruments to a plurality of adjacent bone anchors, each derotator instrument comprising:
a shaft for connecting to a bone anchor;
a handle having a slot; and
an adjustable coupler connecting the shaft and the handle;
adjusting one or more of the adjustable couplers to align at least one of the slots of the plurality of derotator instruments with at least one other slot of the plurality of derotator instruments, wherein adjusting comprises:
moving a first handle into one of a plurality of discrete positions relative to a first shaft via a first adjustable coupler connecting the first shaft and the first handle;
pulling the first handle away from the first shaft to overcome a spring force in the first adjustable coupler;
pivoting the first handle to align a first catch with one of a plurality of slots within the first adjustable coupler; and
releasing the first handle and inserting the first catch into the one of the plurality of slots within the first adjustable coupler; and
inserting an elongate member through two or more slots of the plurality of derotator instruments that are aligned.

13. The method of claim 12, further comprising unlocking the first handle to permit the spring force to be overcome.

14. The method of claim 13, wherein unlocking the first handle comprises rotating a locking collar to an unconstrained position.

15. The method of claim 12, wherein the plurality of discrete positions are located in a plane containing the first handle and the first shaft.

16. A method, comprising:
providing a plurality of derotator instruments, wherein the plurality of derotator instruments comprises a first derotator instrument and a second derotator instrument, wherein each derotator instrument in the plurality of derotator instruments comprises:
a shaft for connecting to a bone anchor;
a handle having a slot; and
an adjustable coupler pivotally connecting the shaft and the handle, wherein the adjustable coupler comprises one or more springs;
pivoting a first handle of the first derotator instrument to align a first slot on a first handle of the first derotator instrument with a second slot on a second handle of the second derotator instrument; and
inserting an elongate member through the first slot and the second slot to maintain an alignment between the first handle and the second handle.

17. The method of claim 16, wherein the adjustable coupler comprises one or more pins.

18. The method of claim 16, wherein the adjustable coupler comprises a locking collar.

* * * * *